United States Patent [19]
Livingston

[11] Patent Number: 5,459,676
[45] Date of Patent: Oct. 17, 1995

[54] SELF CONTAINED DUAL INCLINOMETER SYSTEM

[76] Inventor: J. Tracy Livingston, 324 W. 1120 North, American Fork, Utah 84003

[21] Appl. No.: 160,391

[22] Filed: Dec. 1, 1993

[51] Int. Cl.$^6$ .............................. A61B 5/11; G01B 21/22
[52] U.S. Cl. .............................. 364/559; 33/511; 33/512; 33/534; 73/865.4; 364/550
[58] Field of Search .............................. 33/511, 512, 534; 73/865.4; 364/550, 559

[56] References Cited

U.S. PATENT DOCUMENTS

| | | | |
|---|---|---|---|
| 4,606,133 | 8/1986 | Mills | 33/366 |
| 4,667,413 | 5/1987 | Pitts | 33/344 |
| 4,694,584 | 9/1987 | Mills | 33/366 |
| 4,942,668 | 7/1990 | Franklin | 33/366 |
| 5,107,598 | 4/1992 | Woznow et al. | 33/521 |

OTHER PUBLICATIONS

"ARCON ROM" by Applied Rehabilitation Concepts, Inc.

*Primary Examiner*—Edward R. Cosimano
*Attorney, Agent, or Firm*—Thorpe, North & Western

[57] ABSTRACT

First and second incline sensing devices measure the bending motion of the first body region and the second body region, respectively, in relation to gravity to provide range of motion determinations. With the incline sensing devices held against their respective body regions, a practitioner zeros a digital display provided on the device and the patient performs a range of motion exercise while the practitioner notes the angular value which is continuously updated on a display. The device is small, easily handled, and self contained. Numerous structures are provided to extend the useful life of an internal battery which provides power to all the components. The device utilizes programmed array logic components, which are reliable and consume very little power, to calculate the different between the orientation with respect to gravity of the two incline sensing devices. The difference is shown on a liquid crystal display.

5 Claims, 7 Drawing Sheets

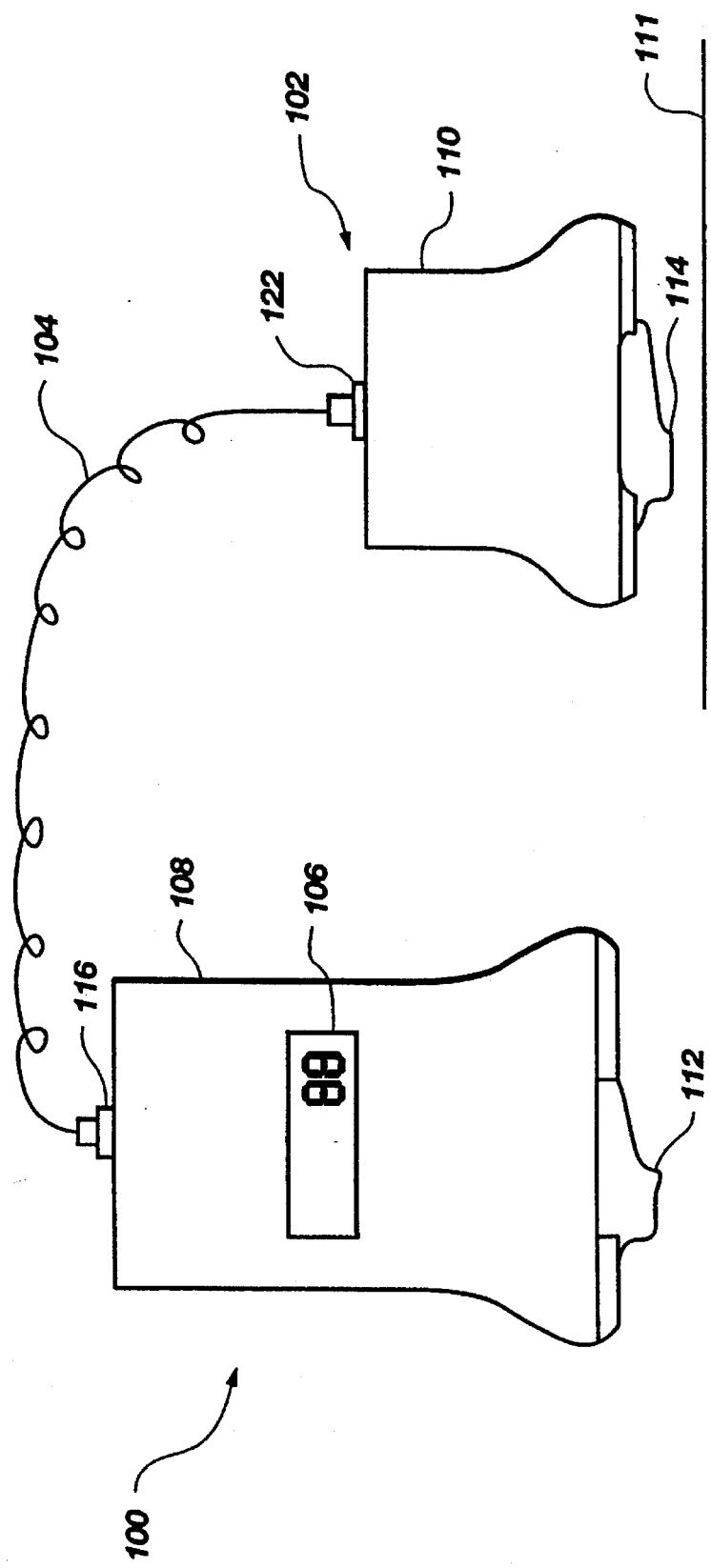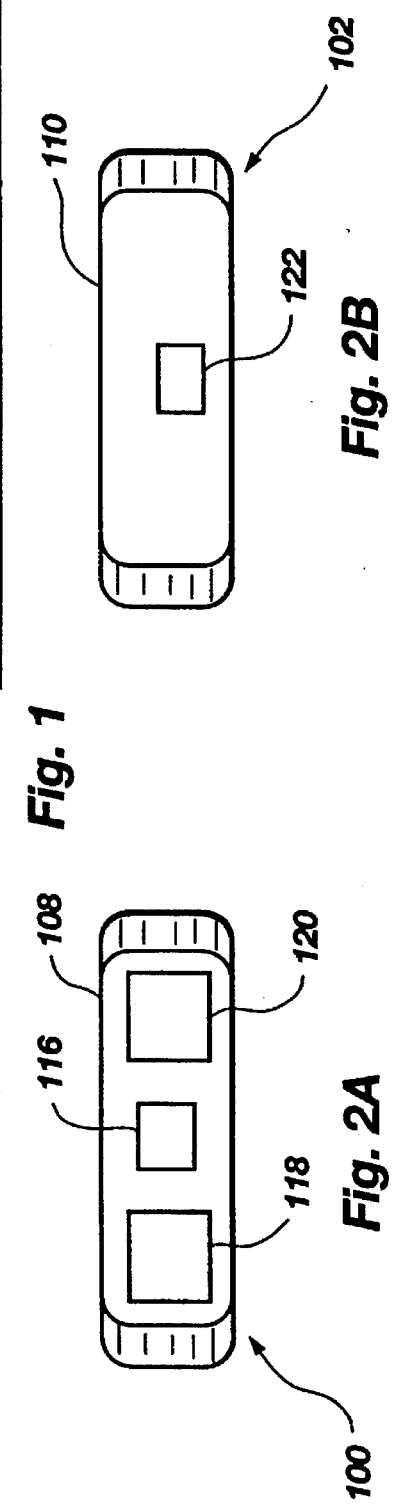

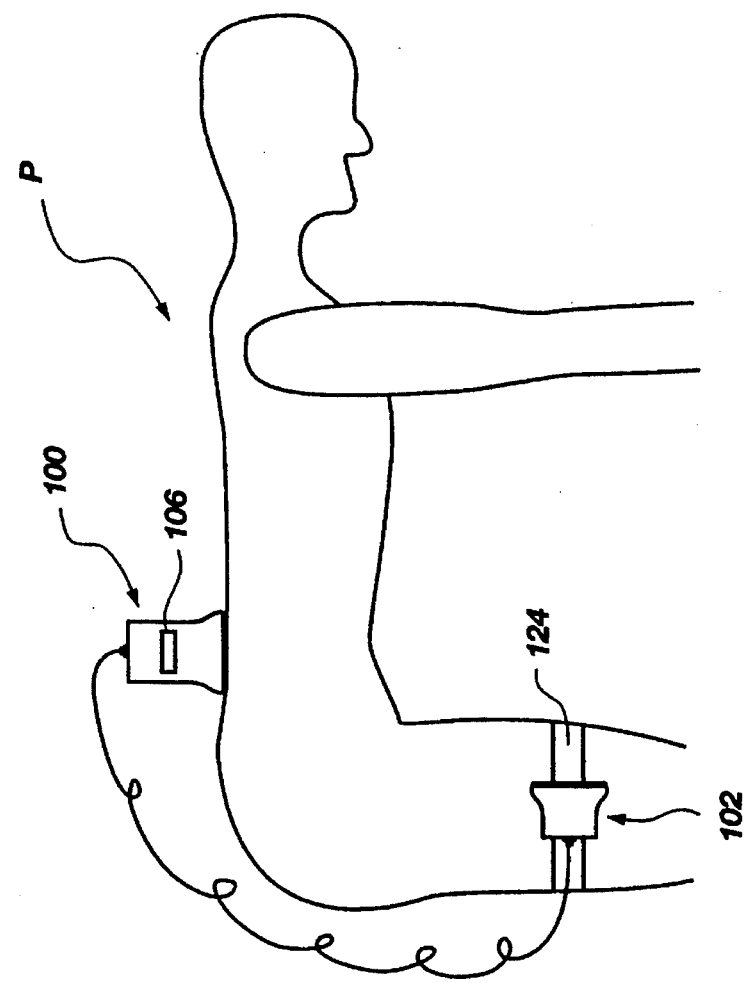
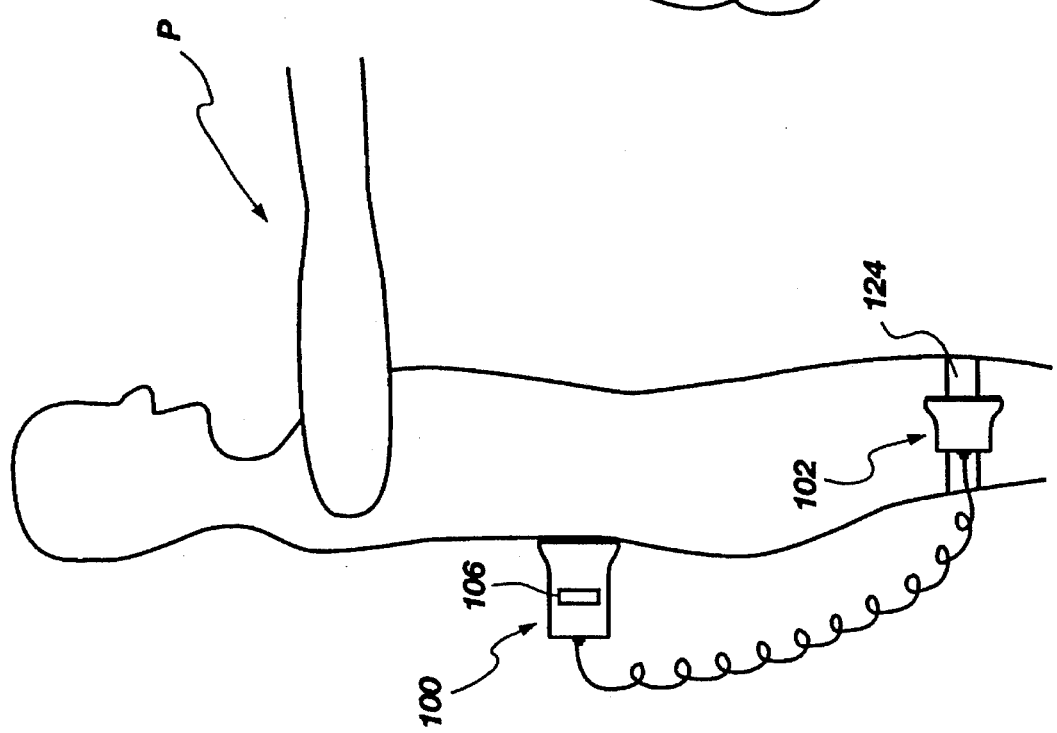

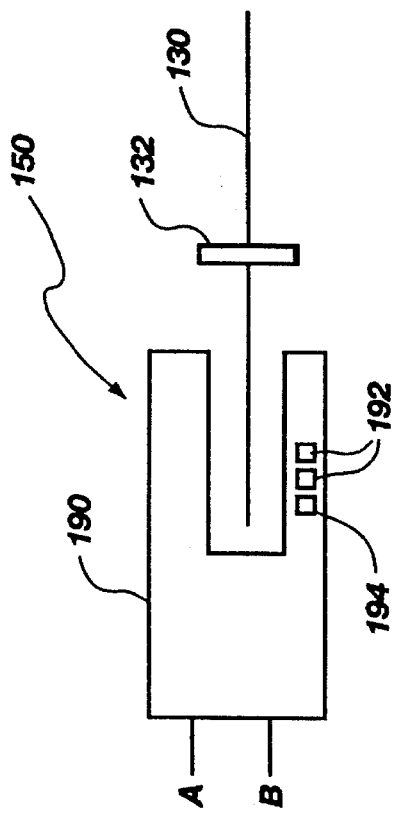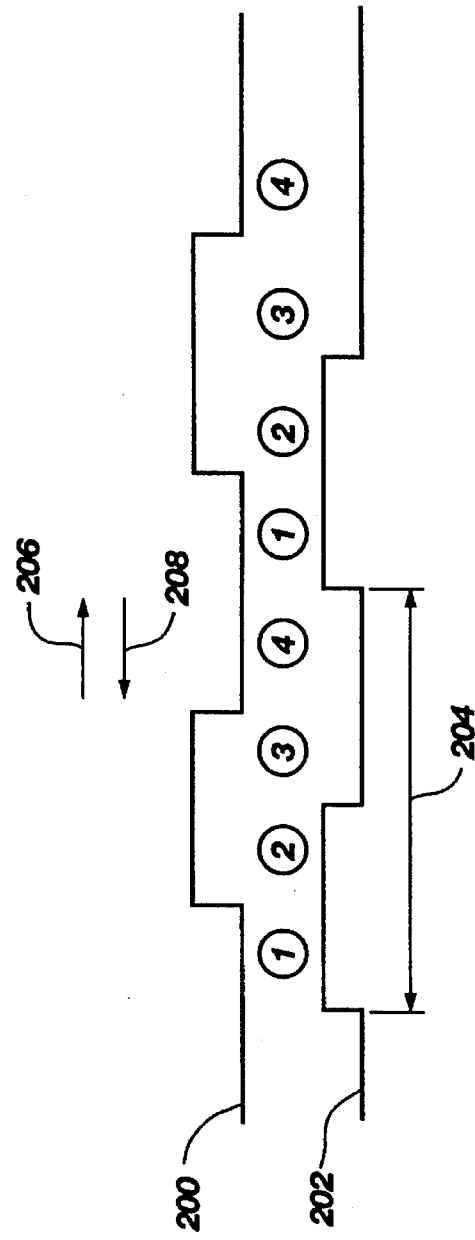

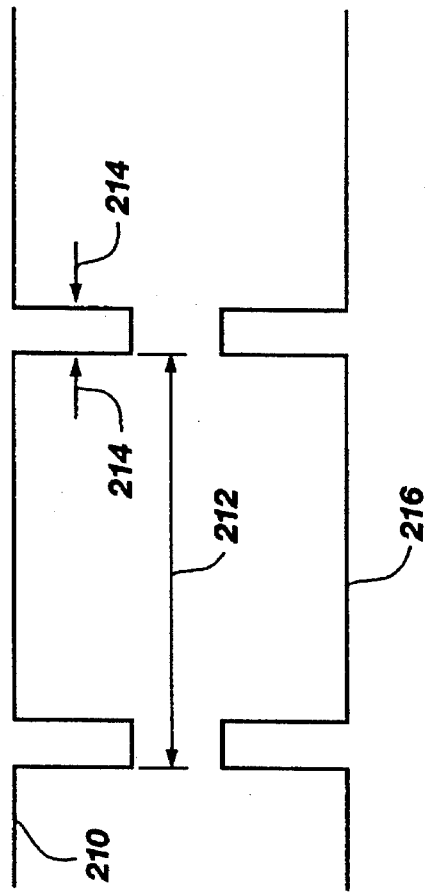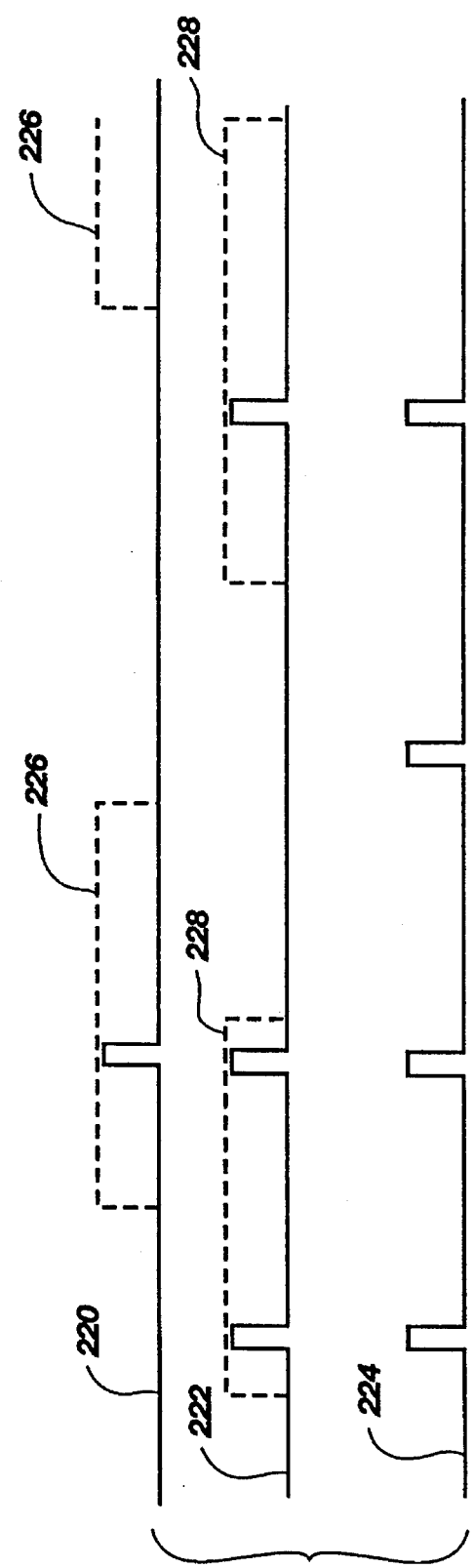
*Fig. 8A*
*Fig. 8B*
*Fig. 8C*

SELF CONTAINED DUAL INCLINOMETER SYSTEM

BACKGROUND

1. The Field of the Invention

This invention relates to devices used to measure the bending motion of various regions of the human body. More particularly, the present invention is related to inclinometers which are used to measure the bending motion of regions of the human body.

2. The Prior Art

Range of motion measurements of various regions of the human body are important to determining the extent to which a patient's mobility has been impaired due to age, injury, or disease. Health care practitioners regularly measure the range of motion possessed by various regions of a person's body. Range of motion is generally measured in units of degrees. For example, if a person is able to rotate his head from shoulder to shoulder, referred to as cervical rotation, then the range of motion for that region of the body is about 90° left and about 90° right.

In the past, mechanical devices known as goniometers were manually manipulated by the medical practitioner in concert with the motion of the body region of interest and an approximation of the range of motion was determined by subtracting beginning and ending readings from a degree scale provided on the goniometer. In an effort to overcome the inaccuracies inherent in the use of goniometers, particularly when used by less experienced practitioners, gravity referenced devices were introduced. Such gravity referenced devices are generally referred to as inclinometers since they measure the motion of the body region with respect to the horizon, or more precisely, with reference to gravity. Such inclinometers consist of three general types: fluid filled devices which are accurate to about 7 degrees; weighted needle devices which are accurate to about 4 degrees; and, electronic devices which are accurate to about 1 degree and provide a digital display making them easy to use.

As the art progressed, even more accurate range of motion measurements were desired by practitioners. It was recognized that the motion of an adjacent body region influences the measurement of the range of motion of another body region of interest. For example, to measure the range of motion for cervical flexion and extension, i.e., bending of the neck forward and backward, any bending of the back will undesirably alter the inclinometer reading since the inclinometer is determining the movement of the neck with reference to gravity without regard to whether the movement of the neck region is due to the bending of the patient's neck or the bending of the patient's back.

In order to find the true range of motion for the patient's neck, the motion of the back must be subtracted from the motion of the patient's neck. Such differential measurements, for example, the difference between the motion of the neck region and the motion of the upper back region, provide the most useful and accurate range of motion determinations.

In order to automatically provide differential range of motion measurements, it has been proposed in the art to utilize two inclinometers connected to a desk top computer. Each of the inclinometers are individually attached to a particular body part, for example, the head and the upper back. Each of the inclinometers are also individually attached to the desk top computer via one or more respective cords. While such an arrangement provides differential range of motion measurements it also presents significant drawbacks.

The cables connecting the inclinometers to the desk top computer are cumbersome; they get in the way during the examination and restrict the distance which the practitioner can move the patient from the desk top computer. Also, the patient must be brought to the desk top computer and its attached inclinometers. The unnecessary movement of patients from one examination room to another examination room is confusing, disruptive, and interferes with the examination of other patients. The desk top computer is generally much more powerful, and thus more expensive, than needed for merely calculating differential range of motion measurements. The expense of the additional components which must be added to a desk top computer further increase the cost.

Another disadvantage is that the practitioner must look away from the patient in order to view the computer screen showing the operation and results of the device. Still further, a desk top computer utilizes line voltages of 100 volts or higher. Thus, medical device standards require that precautions be implemented to isolate the patient from any harmful electrical currents. The precautions taken to ensure electrical isolation of the patient add to the cost and complexity of a dual inclinometer scheme when a desk top computer is used.

In view of the drawbacks and disadvantages found in the current state of the art, it would be an advance in the art to provide a self contained differential inclinometer system which is portable and easy to use.

BRIEF SUMMARY AND OBJECTS OF THE INVENTION

In view of the above described state of the art, the present invention seeks to realize the following objects and advantages.

It is a primary object of the present invention to provide a self contained apparatus for measuring the differential motion of two different regions of a patient's body.

It is also an object of the present invention to provide a system for measuring a differential range of motion between two regions of a patient's body which is small, portable, and convenient to carry.

It is a further object of the present invention to provide a system for measuring the difference between the range of motion of two regions on a patient's body which does not require lengthy cords or cables which interfere with a practitioner's use of the system and examination of the patient.

It is yet another object of the present invention to provide a system for measuring the differential of the motion of two body parts which includes an internal power supply and does not require any connection to an external power source.

It is a still further object of the present invention to provide a system for making differential measurements of the motion of two body parts which consists of only two measuring components which are interconnected with no other components being required.

It is also another object of the present invention to provide an dual inclinometer system for measuring range of motion which does not contain any electrical potentials which could harm a patient.

It is a further object of the present invention to provide system for making differential measurements between different regions of a patient's body which allows the practitioner to keep his attention directed to the patient.

It is another object of the present invention to provide a dual inclinometer system for measuring range of motion in a region of a patient's body which outputs the results in a form more easily perceived by the practitioner.

These and other objects and advantages of the invention will become more fully apparent from the description and claims which follow, or may be learned by the practice of the invention.

The present invention provides a system for measuring the difference in the bending motion a first body region and the bending motion of a second body region of a patient. The difference between the bending motions is automatically displayed without any need for the practitioner to make any calculations.

The preferred embodiments include a first incline sensing means for measuring the bending motion of the first body region in relation to gravity. A second incline sensing means is also similarly provided. One or both of the incline sensing means are attached to respective body regions using a strap means, by the practitioner holding the incline sensing means against the body region, or by some other means which can be devised in the art. With the first incline means held against a first body region and the second incline means held against a second body region, the practitioner zeros a digital display provided on the first housing means, and the patient performs a range of motion exercise while the practitioner notes the angular value which is continuously updated on the display.

Each of the incline sensing means is contained within respective housing means. The housing means is preferably a small and easily handled case which allows convenient use and portability. Each of the incline means preferably comprises an encoder wheel comprising a plurality of optically readable indices, a means for pivotally mounting the encoder wheel to allow rotation of the encoder wheel in a first plane, a means for directing the encoder wheel downward orientation with respect to gravity, and a means for optically sensing the passage of the optically readable indications as said indications pass by a first location as the encoder wheel rotates in the first plane. The encoder wheel is preferably mounted on a shaft having first and second ends with jewel bearings provided at the ends of the shaft.

A calculation means for manipulating the values output from the first and second incline sensing means is provided to calculate the difference between the two values. The calculation means can be comprised of any of now known, or known in the future, components but is preferably comprised of a plurality of programmed array logic devices which are reliable and consume little power. The value arrived at by the calculation means is output to the display means which preferably includes an integral digital counter and a liquid crystal display.

While various structures can be used to interconnect the first incline sensing means and the second incline sensing means, the preferred structure is an electrical cable because of a cable's reliability and infinitesimal power consumption when compared to other wired and wireless arrangements. To provide completely self contained operation, a battery means for providing electrical current to the other components are provided in accordance with the present invention.

A means for strobing power is preferably provided to reduce the power consumed by selected components of the embodiments of the present invention. The means for strobing the power operates at a rate greater than the expected state changes of the incline sensing means, each state change generally indicating an incline of one quarter degree.

Switches are preferably provided to provide a means for holding the value shown on the display means and for providing a means for setting the calculation means to zero and thus zeroing the digital display means. Also preferably provided is a means for dampening the motion of the rotating components of the incline sensing means to reduce the influence of rotational oscillations on the displayed value. The means for dampening preferably includes a means for generating a magnetic field, for example, a permanent magnet mounted on a metallic, nonmagnetic plate, which will oppose rotation in either a clockwise or counter clockwise direction. Other arrangements, such as those carried out digitally by the calculation means, can also function as the dampening means.

BRIEF DESCRIPTION OF THE DRAWINGS

In order to better appreciate how the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which:

FIG. 1 is a front view of one presently preferred embodiment of the present invention.

FIGS. 2A and 2B are top views of the presently preferred embodiment represented in FIG. 1.

FIGS. 3A and 3B are diagrammatic representations of the embodiment of the present invention represented in FIG. 1 in place on a patient.

FIG. 6 is a diagrammatic representation of the components which encode the inclination of the presently preferred embodiment of the present invention.

FIG. 7 is a timing diagram of the showing the output of the encoder components represented in FIG. 6.

FIGS. 8A–8C are timing charts showing the strobing of power to the encoder components.

DETAILED DESCRIPTION OF THE PREFERRED EMBODIMENTS

Figure 4A:
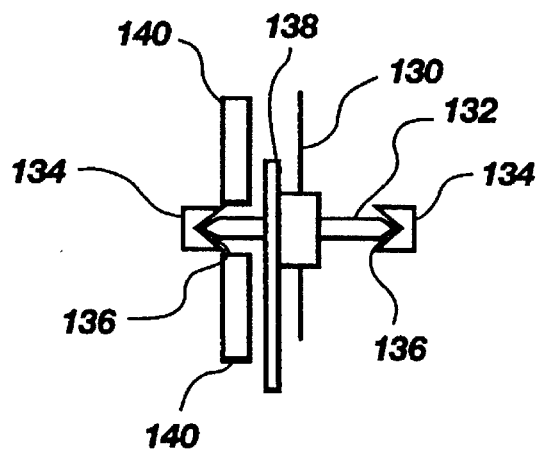
FIGS. 4A–4C are representations of the encoder wheel and oscillation damping assembly of the presently preferred embodiment of the present invention.

Reference will now be made to the drawings wherein like structures will be provided with like reference designations.

FIG. 1 provides a representation of one presently preferred embodiment of the present invention. The self contained dual inclinometer system represented in FIG. 1 includes a master sensor and display unit, generally represented at 100, and a slave sensor unit, generally represented at 102. The master sensor and display unit 100 and the slave sensor unit 102 each include a housing 108 and 110, respectively.

The master sensor and display unit 100 and the slave sensor unit 102 are each small and light weight and can be easily stored in a practitioner's coat pocket. It is preferred that the master sensor and display unit 100 have dimensions not greater than about 6 inches high, about 3 inches wide, and about 1.5 inches thick and most preferably not greater than about 4 inches high, about 2.5 inches wide, and about 0.75 inches thick.

Its small size and light weight allows the dual inclinometer system of the present invention to be moved from patient to patient whether the patients are located in different rooms in the same building or far apart from each other. In contrast, the previously available dual inclinometers required a cumbersome wired connection to a bulky desk top computer.

Also represented in FIG. 1 is a coiled interconnecting cord 104 which interconnects the master sensor and display unit 100 and the slave sensor unit 102. The interconnecting cord 104 provides a reliable and convenient means for interconnecting the master sensor and display unit 100 and the slave sensor unit 102. It will be appreciated that it is within the scope of the present invention to utilize other wired or wireless, e.g., radio frequency or optical, links between the master sensor and display unit 100 and the slave sensor unit 102. It is preferred that the interconnecting cord 104 be a coiled cord having a connector (not completely shown) at each end. The connectors are preferably ones which are compatible with the RJ-xx series of connectors as are well known in the art.

Still referring to FIG. 1, a display 106 is provided on the master sensor and display unit 100. The display 106 is preferably a digital liquid crystal display which consumes very little power as is known in the art. The display 106 is preferably provided only on the master sensor and display unit 100. It is also within the scope of the present invention to place the display 106 on the slave sensor unit 102, on both the slave sensor unit 102 and the master sensor and display unit 100, and/or couple the master sensor and display unit 100 to another nearby monitor, for example a desk top computer when the computing power and memory of a desk top computer is required.

As shown in FIG. 1, the master sensor and display unit 100 and the slave sensor unit 102 are each provided with magnetic feet 112 and 114. The magnetic feet 112 and 114 are particularly adapted to releasably hold a rail 111 in place. The rail 111, or a similar structure, is used by a practitioner to help position the master sensor and display unit 100 and/or the slave sensor unit 102 while performing a range of motion evaluation.

FIGS. 2A and 2B provide top views of the master sensor and display unit 100 and the slave sensor unit 102, respectively. Provided on the master sensor and display unit 100 is a jack 116 into which one end of the interconnecting cord (104 in FIG. 1) is inserted. The jack 116 is preferably one compatible with the RJ-xx series standard to allow easy insertion and removal of the interconnecting cord 104. Similarly, as shown in FIG. 2B, an RJ-xx series compatible jack 122 is provided on the slave sensor unit 102. It will be appreciated that there will be occasions when the master sensor and display unit 100 will be used without the slave sensor unit 102 so easy removal of the interconnecting cord 104 can be accomplished.

Represented in FIG. 2A are a zero switch 118 and a hold switch 120. The zero switch 118 functions to reset the display (106 in FIG. 1) to zero at the start of a measurement. The hold switch 120 functions to freeze the value shown on the display (106 in FIG. 1) to allow a practitioner ample time to note or record the value.

FIGS. 3A and 3B illustrate one preferred use of the described embodiment of the present invention to measure hip flexion and extension range of motion. In FIG. 3A a patient P is shown in a standing position. The slave sensor unit 102 has been attached to the patient's P thigh using an adjustable strap 124. The master sensor and display unit 100 is placed on the patient's P back and held there by a practitioner conducting the examination. With the patient in the position shown in FIG. 3A, the practitioner momentarily presses the zero switch (118 FIG. 2A) and the patient bends over, for example to the position shown in FIG. 3B. The practitioner can then press the hold switch (120 in FIG. 2B) if desired to hold the value shown on the display 106 and record the value shown on the display 106 of the master sensor and display unit 100.

As will be fully appreciated after considering this description, the display 106 shows a value which is the difference between the incline sensed by master sensor and display unit 100 and the incline sensed by slave sensor unit 102. By displaying a differential value the influence of leg movement is removed from the value and an accurate value for hip flexion is obtained. Other range of motion measurements, for example cervical range of motion, thoracic range of motion, lumbar range of motion, and extremity range of motion can also be performed.

Figure 4B:
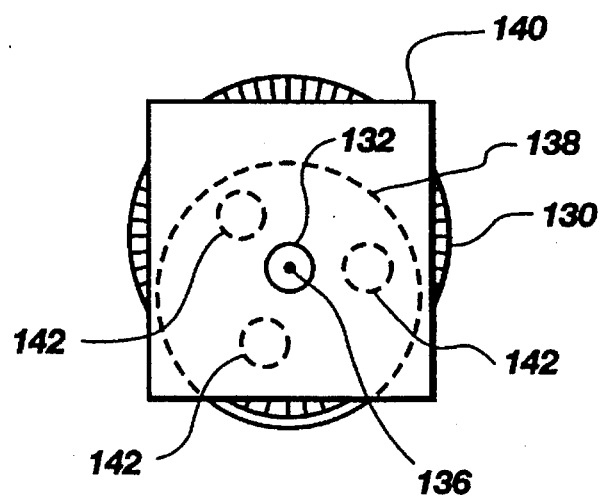
Figure 4C:
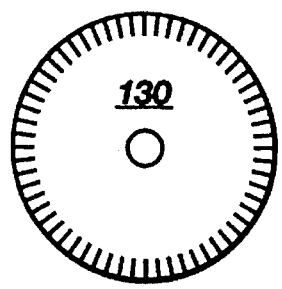

Reference will next be made to FIGS. 4A–4C which diagrammatically represent the mechanical components used to measure the incline of the master sensor and display unit 100 and the slave sensor unit 102. Represented in FIGS. 4A–4C is an encoder wheel 130. FIG. 4C shows the circular encoder wheel 130 and a portion of optical markings placed about its circumference at every degree. Thus the encoder wheel 130 includes 360 radially arranged indicia about its circumference. It is preferred that the encoder wheel 130 have a diameter which is less then one inch but any size encoder wheel 130 which is suitable can be used within the scope of the present invention.

The encoder wheel 130 is fixed to a eccentrically mounted metal disk 138, preferably fabricated from a non-magnetic metal such as aluminum. The eccentrically mounted metal disk 138 is fixed to a shaft 132 which is also preferably fabricated from a nonmagnetic material. The shaft 132 is provided with jewel pivot points 136 which are received into bearing cups 134. The use of jewel bearings provides significant benefits not previously obtained in a medical inclinometer. The resulting low friction operation also provides accuracy not previously obtainable.

Referring still to FIGS. 4A and 4B, with the eccentrically mounted metal disk 138 fixed on the shaft 132, the encoder wheel 130 will maintain its orientation with respect to gravity as the housing (108 or 110 in FIG. 1) rotates about it.

In order to minimize undesirable pendulum oscillation of the encoder wheel 130 as the device is moved, a plate 140, preferably fabricated from nonmagnetic material such as aluminum (shown best in FIGS. 4A and 4B), is provided with three permanent magnets 142, preferably samarium cobalt permanent magnets or some other similarly functioning magnet, affixed thereto and in close proximity to the eccentrically mounted metal disk 138. The magnets 142 function to induce a current in the eccentrically mounted metal disk 138 when rotated relative to each other. The resulting magnetic field functions to dissipate the oscillations of the encoder wheel 130 and to dampen its movement. Dampening the movement of the encoder wheel 130 provides more accurate measurements.

Figure 5:
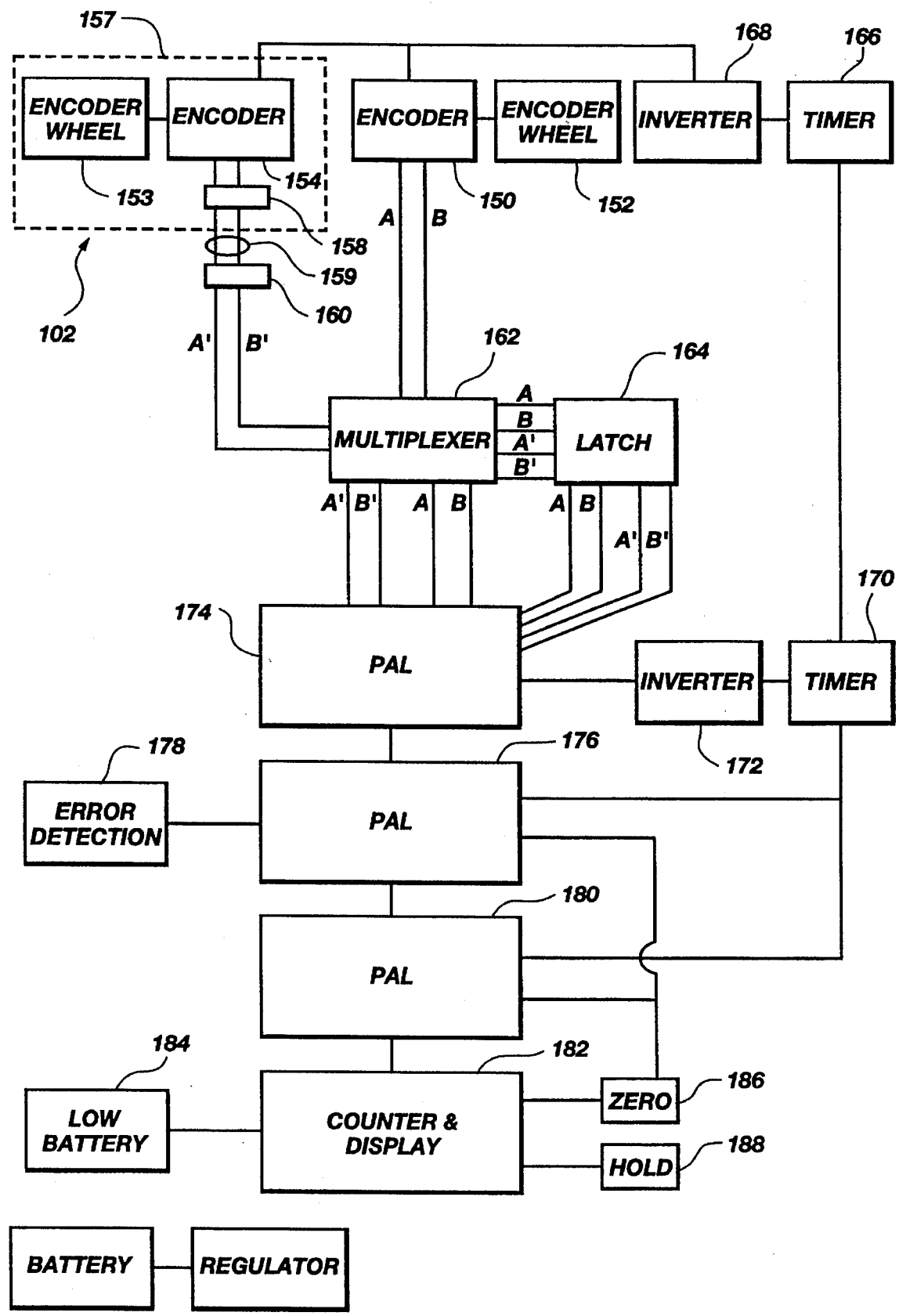
FIG. 5 is a block diagram representing the major functional component of the presently preferred embodiment of the present invention.

Reference will now be made to FIG. 5. FIG. 5 is a block diagram representing the major functional components of the preferred embodiment of the present invention. All of the components represented in FIG. 5 are contained within the housing (108 in FIG. 1) of the master sensor and display unit 100 with the exception of those shown within the box 157 which are contained within the housing (110 in FIG. 1) of the slave sensor unit 102.

An encoder wheel contained within the master sensor and display unit 100 is represented at 152. As the encoder wheel 152 rotates, the optical markings (see FIG. 3C) pass through an encoder 150 which outputs an electrical signal. The signal which is output from the encoder 150 corresponds to the angular rotation of the encoder wheel 152. The slave sensor unit 102 is provided with a similar encoder wheel 153 and an encoder 154. The output from the encoder 154 is conveyed to a jack 158, through an interconnecting cord 159, to a jack 160 where the signal is relayed to components contained within the master sensor and display unit 100.

FIG. 6 provides a diagrammatic cross sectional representation of the encoder wheel 130 and the shaft 132 as well as the encoder, generally represented at 150, which includes a C shaped encoder body 190 into which the encoder wheel 130 is received. The encoder 150 is preferably one available from Hewlett-Packard and known in the art as part of the HEDS-9100 series and also includes the appropriate HEDS-5100 codewheel option available from Hewlett-Packard. Further information regarding the preferred encoder 150 is available from Hewlett-Packard in the publication entitled Two Channel Optical Incremental Encoder Module 11 mm Optical Radius which is now incorporated herein by reference in its entirety. It will be appreciated that other devices known in the art can also be used as the encoder 150.

The encoder 150 outputs a signal which corresponds to the number of degrees through which the encoder wheel 130 rotates after the zero switch (186 in FIG. 5) is activated. The encoder body 190 accommodates an LED 194 and a lens (not illustrated in FIG. 6) to focus the light from the LED 194 onto the encoder wheel 130. The encoder body 190 accommodates photo collectors 192 and appropriate circuitry to provide outputs which correspond to when the photo collectors 192 sense the optical marks on the encoder wheel 130 (see FIG. 3c).

Still referring to FIG. 6, as an optical mark on the encoder wheel 130 passes by the photo collectors 192, output from the corresponding collector 192 goes low and returns to a high state when no optical mark is detected. The respective outputs from the encoder 150 are referred to as A and B. The encoder 150 provides a quadrature output, i.e., the output is phase-shifted according to the direction of movement of the wheel. Encoder 154 represented in FIG. 5 operates similarly and provides outputs which are represented in FIG. 5 as A' and B'.

FIG. 7 provides an exemplary timing diagram for the outputs of the encoder 150. The waveform 200 represents the A output of the encoder 150 while the waveform 202 represents the output B of the encoder 150. Arrow 206 represents clockwise movement of the encoder wheel 130 while arrow 208 represents counter clockwise movement of the encoder wheel 130. Arrow 204 represents one degree of rotation of the encoder wheel 130. From FIG. 7, it can be seen that output A leads output B during clockwise rotation of the encoder wheel 130 and that output B leads output A during counter clockwise rotation of the encoder wheel 130.

For each degree of rotation of the encoder wheel 130, there are four unique states. Each of the states is identified in FIG. 7 by the bubbles numbered 1, 2, 3, and 4 shown adjacent to the waveforms 200 and 202. At the time the zero switch (186 in the block diagram of FIG. 5) is activated, which of the four states is current is determined. The circuitry included in the master sensor and display unit 100, represented in FIG. 5 and which will be discussed shortly, requires that four state changes must occur before a count of one degree and a direction are recognized. Thus, it will be appreciated that from the states (1 through 4) which are determined from the outputs of the encoder 150, the direction of rotation of the encoder wheel 130 and the amount of rotation of the encoder wheel 130 can be determined. It will be appreciated that the encoder wheel 153 and the encoder 154 included in the slave sensor unit 102 represented in FIG. 5 is structured and operates in substantially the same way.

It will be appreciated that to provide the present invention with the greatest possible portability, the components included within the master sensor and display unit 100 and the slave sensor unit 102 are powered by a battery 196 through a DC to DC power convertor 198 as represented in FIG. 5 to provide 4 volts DC. The battery 196 can preferably be a small battery which nominally provides about 1.5 volts, for example, a AAA size alkaline cell. The DC to DC convertor can preferably be one available from Linear Technology and referred to in the art as TL1110. It will be appreciated, however, that many other components can perform the functions of the battery 196 and the DC to DC power convertor 198. A low battery detection means 184 is also provided as known in the art.

In order to operate the master sensor and display unit 100 and the slave sensor unit 102 for a long period of time, preferably up to 100 hours, without requiring a change of the battery 196, the present invention provides components to extend the life of the battery 196 as will now be explained by referring to FIG. 5 and FIGS. 8–9.

Using the above described preferred encoders 150, the life of battery 196 would be severely limited if power were supplied to the encoders 150 continuously. For example, when the preferred components for encoders 150 are used, the power consumption exceeds 40 milliamps. Thus, a typical AAA size cell would discharge in as little as two hours. In order to greatly extend the life of the battery 196, the power to the encoder 150 is strobed on and off. Importantly, the present invention provides that the strobing rates exceeds the rate at which state changes occur (see FIG. 7) and thus the present invention provides error free operation under typical circumstances. Preferably, the strobing rate is greater than about 10 KHz but is most preferably much higher as will shortly be appreciated.

Referring again to FIG. 5, power strobing is timed by a timer 166. Timer 166 is known in the art as a 555 timer. Timer 166 is preferably contained in one integrated circuit available from Maxim Integrated Products and known in the art as an ICM7556 timer which contains two independent 555 timers in one integrated circuit, the function of the second 555 timer being explained shortly. As known in the art, by adjusting the values of resistive and capacitive components positioned externally to the integrated circuit, the frequency (both the period and the duration of the pulses) which is output from the 555 timer can be set to the desired value.

In FIG. 8A, waveform 210 shows the preferred output from the timer 166. Arrow 212 shows the preferred period of the output of the timer 166 is about 80 microseconds while arrow 214 shows the preferred duration of the output is about 6 microseconds.

The output of the timer 166 is directed to an invertor 168. The invertor 168 is preferably contained in one integrated circuit available from Motorola and known in the art as an 74HC04A hex invertor. The invertor 168 preferably outputs a waveform 216 as shown in FIG. 8B which is preferably the complement of the waveform 210 represented in FIG. 8A.

It will be appreciated that the described arrangement reduces power consumption by over 90% of what would otherwise be consumed by the same components. It is preferred that the components used in the master sensor and display unit 100 and slave sensor unit 102 be selected to minimize power consumption, for example, many of the preferred components utilize low power CMOS technology. This low power consumption allows the embodiments of the present invention to be self contained, light weight, and small resulting in portability not previously available in the art for a dual inclinometer suitable for conducting range of motion measurements on a patient.

The waveform 216 represented in FIG. 8B powers the encoders 150 and 154 represented in FIG. 5. FIG. 8C will now be referred to explain the resulting A and B outputs of the encoders 150 and 154 as a result of the strobing of the power represented in FIG. 8B.

In FIG. 8C, waveform 220 represents the A output of encoders 150 and 154 while waveform 222 represents the B output of the encoders 150 and 154. Outline images 226 and 228 shown in FIG. 8C represent the A and B outputs of the encoders 150 and 154, respectively, if the power to the encoders 150 and 154 were not strobed and are substantially similar to the waveforms 200 and 202 represented in FIG. 7. Waveform 224 represents the power input to the encoders 150 and 154 which produces the resulting waveforms 220 and 222. As represented in FIG. 8C, the A and B outputs of the encoders 150 and 154 go high only when the power strobe 224 is high and outputs A and B would be high if continuously powered.

As represented in FIG. 5, the output of the encoder 150 is passed to a multiplexer 162. The multiplexer 162 is preferably an integrated circuit available from Motorola and referenced in the art as MC14551B quad 2 channel analog multiplexer/demultiplexer. The multiplexer 162 selectively diverts any signals output from the encoder 150 to the jack 160 in order to allow an external device, such as a personal computer, to access the internal signals within the master sensor and display unit 100. Those skilled in the art, using the information provided herein, will appreciate the arrangement of components necessary to interface a computer with the master sensor and display unit 100. Also, in many cases there will not by any need to interface the master sensor and display unit 100 to a computer and thus multiplexer 162 can be omitted.

If the master sensor and display unit 100 is connected to a computer (not represented in the figures), the multiplexer 162 automatically diverts the signals output from the encoder 150 to the jack (116 in FIG. 2). If the master sensor and display unit 100 is not attached to a computer, the multiplexer 162 feeds the outputs of the encoders 150 and 154 to the inputs of a first PAL 174 (programmed array logic device) and to the inputs of a latch 164. If the slave sensor unit 102 is not attached, the lines which would otherwise receive the outputs of the encoder 154 contained within the slave sensor unit 102 remain idle.

The latch 164 is transparent to the inputs received from the A and B outputs of the encoders 150 and 154 when the zero switch 186 is activated. When the zero switch 186 is released, the states of the outputs of the latch 164 are held. The outputs of the latch 164 are conducted to the inputs of the first PAL 174. The outputs of the latch 164 feed into the first PAL and provide a reference logic state for the first PAL's output according to the four state change criteria as explained earlier in connection with FIG. 7.

Still referring to FIG. 5, the PAL 174 can be any one of a number of devices which are well known in the art. It is preferred that the PAL 174 be one available from Advanced Micro Devices and referred to in the art as PALCE16V8Z-25 zero power 20 pin EE CMOS universal programmable array logic. Further information regarding the preferred component for the PAL 174 is available in publication no. 13061 (January 1992) from Advanced Micro Devices which is now incorporated herein by reference in its entirety. As in the case of all components used in the master sensor and display unit 100 and the slave sensor unit 102, any alternative devices selected to carry out the functions of the PAL 174 should be chosen for low power consumption. It will be appreciated that the use of the preferred programmed array logic devices provides very reliable operation combined with very low power consumption.

The outputs of the first PAL 174 change only on the rising edge of a clock input pulse received from invertor 172. Thus, in order for data to be validly received, the power to the encoders 150 and 154 must be strobed on and sufficient time elapsed for data present on outputs of the encoders 150 and 154 to stabilize before the clock pulse is presented to the first PAL 174, as well as to a second PAL 176 and to a third PAL 180.

The clock pulse provided to the first PAL 174 is created by triggering timer 170 by the rising edge of the power strobe (see waveform 210 in FIG. 8A) output from the timer 166. The second timer is preferably contained within the same integrated circuit as the first timer 166 as explained earlier. The external resistance and capacitive components are selected to provide a clock pulse 232 represented in FIG. 9A. The clock pulse 232 is that which is output from an invertor 172.

Figure 9A:
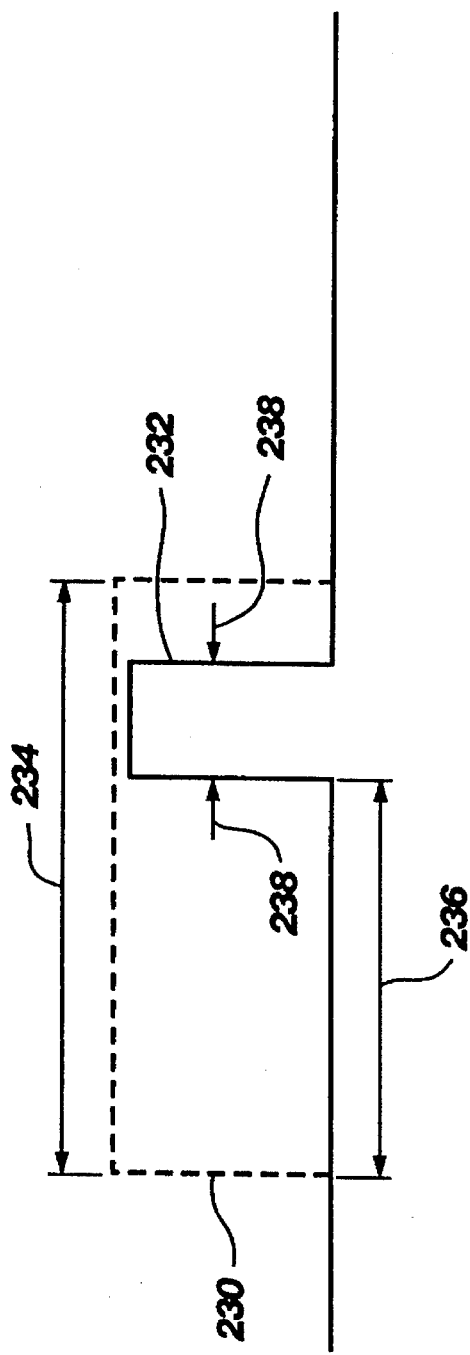
FIGS. 9A and 9B are timing charts showing the result of the power strobing represented in FIGS. 8A–8C on the output of the encoder components.

In FIG. 9A, a waveform 230 (shown in outline) represents the strobing of the power to the encoders 150 and 154. The arrow 234 represents the length of the power strobe which is preferably about six microseconds (see FIG. 8A). The clock pulse 232 which is output from the timer 170 is started about four microseconds after the rising edge of the power strobe waveform 234, as indicated by arrow 236. The clock pulse 232 is preferably about one microseconds wide as indicated by arrows 238.

Figure 9B:
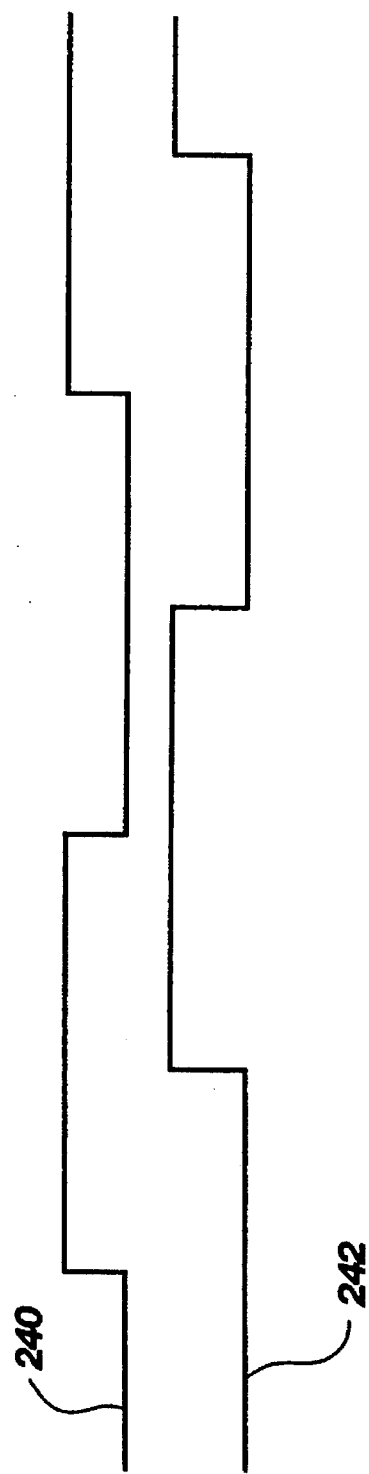

The output lines of the first PAL 174 corresponding to the encoder 150 and 154 outputs A and B do not go high and low with the power strobe but now appear as shown in FIG. 9B. FIG. 9B provides a exemplary representation of two waveforms 240 and 242 which represent two of the outputs of the first PAL corresponding to the data present on outputs A and B of encoder 150 or 154. Changes in the output of the first PAL 174 as a function of input occur only on the rising clock pulse provided by the timer 170 and the invertor 172.

After the decoding by the first PAL 174, the outputs of both encoders 150 and 154 are fed into the second PAL 176. The second PAL determines when one of the encoder wheels, encoder wheel 152 in the master sensor and display unit 100 or encoder wheel 153 in the slave sensor unit 102, has rotated one degree. The second PAL 176 generates two signals (each signal either high or low). One the outputs of the second PAL 176 acts to provide a "degree count" when an encoder wheel rotates through one degree. The other output of the second PAL 176 acts to indicate the direction of rotation of an encoder wheel. The outputs of the second PAL 176 will remain in the indicated state until the next clock pulse is output from the invertor 172.

It is preferred that the second PAL 176 be one available from Advanced Micro Devices and referred to in the art as PALCE22V10Z-25 zero power 24 pin EE CMOS versatile PAL device. Further information regarding the preferred component for the PAL 176 is available in publication no. 15700 (Rev. A, January 1992) from Advanced Micro Devices which is now incorporated herein by reference in its entirety. It is preferred that the embodiment of the present invention also include an error detection structure 178.

Listed below is a logic chart captioned "SHFTENC.DOC MASTERSHAFT ENCODE TRUTH TABLE which shows the names assigned to the inputs and the various states of the inputs of the second PAL 176 and the resulting output states with the names assigned to those outputs. Those skilled in the art will be familiar with the techniques and equipment necessary to program the second PAL 176.

Provided below in Glossary A are the meanings of the names assigned to the inputs and the outputs listed below:

SHFTENC.DOC
MASTERSHAFT ENCODER TRUTH TABLE:

| MP2 | MP1 | MP0 | SERR | MDA | MDB | MN2 | MN1 | MN0 | MBLIP* | MERR |
|---|---|---|---|---|---|---|---|---|---|---|
| 0 | 0 | 0 | 0 | 0 | 0 | 0 | 0 | 0 | 1 | 0 |
| 0 | 0 | 0 | 0 | 0 | 1 | 1 | 0 | 1 | 1 | 0 |
| 0 | 0 | 0 | 0 | 1 | 0 | 0 | 1 | 0 | 1 | 0 |
| 0 | 0 | 0 | 0 | 1 | 1 | 1 | 0 | 0 | 1 | 1 |
| 0 | 0 | 0 | 1 | X | X | 1 | 0 | 0 | 1 | 0 |
| 0 | 0 | 0 | 1 | X | X | 1 | 0 | 0 | 1 | 0 |
| 0 | 0 | 0 | 1 | X | X | 1 | 0 | 0 | 1 | 0 |
| 0 | 0 | 0 | 1 | X | X | 1 | 0 | 0 | 1 | 0 |
| 0 | 0 | 1 | 0 | 0 | 0 | 0 | 0 | 0 | 0 | 0 |
| 0 | 0 | 1 | 0 | 0 | 1 | 0 | 0 | 1 | 1 | 0 |
| 0 | 0 | 1 | 0 | 1 | 0 | 1 | 0 | 0 | 1 | 1 |
| 0 | 0 | 1 | 0 | 1 | 1 | 0 | 1 | 1 | 1 | 0 |
| 0 | 0 | 1 | 1 | X | X | 1 | 0 | 0 | 1 | 0 |
| 0 | 0 | 1 | 1 | X | X | 1 | 0 | 0 | 1 | 0 |
| 0 | 0 | 1 | 1 | X | X | 1 | 0 | 0 | 1 | 0 |
| 0 | 0 | 1 | 1 | X | X | 1 | 0 | 0 | 1 | 0 |
| 0 | 1 | 0 | 0 | 0 | 0 | 0 | 0 | 0 | 1 | 0 |
| 0 | 1 | 0 | 0 | 0 | 1 | 1 | 0 | 0 | 1 | 1 |
| 0 | 1 | 0 | 0 | 1 | 0 | 0 | 1 | 0 | 1 | 0 |
| 0 | 1 | 0 | 0 | 1 | 1 | 0 | 1 | 1 | 1 | 0 |
| 0 | 1 | 0 | 1 | X | X | 1 | 0 | 0 | 1 | 0 |
| 0 | 1 | 0 | 1 | X | X | 1 | 0 | 0 | 1 | 0 |
| 0 | 1 | 0 | 1 | X | X | 1 | 0 | 0 | 1 | 0 |
| 0 | 1 | 0 | 1 | X | X | 1 | 0 | 0 | 1 | 0 |
| 0 | 1 | 1 | 0 | 0 | 0 | 1 | 0 | 0 | 1 | 1 |
| 0 | 1 | 1 | 0 | 0 | 1 | 0 | 0 | 1 | 1 | 0 |
| 0 | 1 | 1 | 0 | 1 | 0 | 0 | 1 | 0 | 1 | 0 |
| 0 | 1 | 1 | 0 | 1 | 1 | 0 | 1 | 1 | 1 | 0 |
| 0 | 1 | 1 | 1 | X | X | 1 | 0 | 0 | 1 | 0 |
| 0 | 1 | 1 | 1 | X | X | 1 | 0 | 0 | 1 | 0 |
| 0 | 1 | 1 | 1 | X | X | 1 | 0 | 0 | 1 | 0 |
| 0 | 1 | 1 | 1 | X | X | 1 | 0 | 0 | 1 | 0 |
| 1 | 0 | 0 | 0 | 0 | 0 | 1 | 0 | 0 | 1 | 1 |
| 1 | 0 | 0 | 0 | 0 | 1 | 1 | 0 | 0 | 1 | 1 |
| 1 | 0 | 0 | 0 | 1 | 0 | 1 | 0 | 0 | 1 | 1 |
| 1 | 0 | 0 | 0 | 1 | 1 | 1 | 0 | 0 | 1 | 1 |
| 1 | 0 | 0 | 1 | X | X | 1 | 0 | 0 | 1 | 0 |
| 1 | 0 | 0 | 1 | X | X | 1 | 0 | 0 | 1 | 0 |
| 1 | 0 | 0 | 1 | X | X | 1 | 0 | 0 | 1 | 0 |
| 1 | 0 | 0 | 1 | X | X | 1 | 0 | 0 | 1 | 0 |
| 1 | 0 | 1 | 0 | 0 | 0 | 0 | 0 | 0 | 1 | 0 |
| 1 | 0 | 1 | 0 | 0 | 1 | 1 | 0 | 1 | 1 | 0 |
| 1 | 0 | 1 | 0 | 1 | 0 | 1 | 0 | 0 | 1 | 1 |
| 1 | 0 | 1 | 0 | 1 | 1 | 1 | 1 | 1 | 1 | 0 |
| 1 | 0 | 1 | 1 | X | X | 1 | 0 | 0 | 1 | 0 |
| 1 | 0 | 1 | 1 | X | X | 1 | 0 | 0 | 1 | 0 |
| 1 | 0 | 1 | 1 | X | X | 1 | 0 | 0 | 1 | 0 |
| 1 | 0 | 1 | 1 | X | X | 1 | 0 | 0 | 1 | 0 |
| 1 | 1 | 0 | 0 | 0 | 0 | 0 | 0 | 0 | 0 | 0 |
| 1 | 1 | 0 | 0 | 0 | 1 | 1 | 0 | 0 | 1 | 1 |
| 1 | 1 | 0 | 0 | 1 | 0 | 1 | 1 | 0 | 1 | 0 |
| 1 | 1 | 0 | 0 | 1 | 1 | 1 | 1 | 1 | 1 | 0 |
| 1 | 1 | 0 | 1 | X | X | 1 | 0 | 0 | 1 | 0 |
| 1 | 1 | 0 | 1 | X | X | 1 | 0 | 0 | 1 | 0 |
| 1 | 1 | 0 | 1 | X | X | 1 | 0 | 0 | 1 | 0 |
| 1 | 1 | 0 | 1 | X | X | 1 | 0 | 0 | 1 | 0 |
| 1 | 1 | 1 | 0 | 0 | 0 | 1 | 0 | 1 | 1 | 1 |
| 1 | 1 | 1 | 0 | 0 | 1 | 1 | 0 | 0 | 1 | 0 |

-continued

| | | | | | | | | | | |
|---|---|---|---|---|---|---|---|---|---|---|
| 1 | 1 | 1 | 0 | 1 | 0 | 1 | 1 | 1 | 1 | 0 |
| 1 | 1 | 1 | 0 | 1 | 1 | 1 | 1 | 0 | 1 | 0 |
| 1 | 1 | 1 | 1 | X | X | 1 | 0 | 0 | 1 | 0 |
| 1 | 1 | 1 | 1 | X | X | 1 | 0 | 0 | 1 | 0 |
| 1 | 1 | 1 | 1 | X | X | 1 | 0 | 0 | 1 | 0 |
| 1 | 1 | 1 | 1 | X | X | 1 | 0 | 0 | 1 | 0 |

SLAVE SHAFT ENCODER TRUTH TABLE:

| SP2 | SP1 | SP0 | MERR | SDA | SDB | SN2 | SN1 | SN0 | SBLIP* | SERR |
|---|---|---|---|---|---|---|---|---|---|---|
| 0 | 0 | 0 | 0 | 0 | 0 | 0 | 0 | 0 | 1 | 0 |
| 0 | 0 | 0 | 0 | 0 | 1 | 1 | 0 | 1 | 1 | 0 |
| 0 | 0 | 0 | 0 | 1 | 0 | 0 | 1 | 0 | 1 | 0 |
| 0 | 0 | 0 | 0 | 1 | 1 | 1 | 0 | 0 | 1 | 1 |
| 0 | 0 | 0 | 1 | X | X | 1 | 0 | 0 | 1 | 0 |
| 0 | 0 | 0 | 1 | X | X | 1 | 0 | 0 | 1 | 0 |
| 0 | 0 | 0 | 1 | X | X | 1 | 0 | 0 | 1 | 0 |
| 0 | 0 | 0 | 1 | X | X | 1 | 0 | 0 | 1 | 0 |
| 0 | 0 | 1 | 0 | 0 | 0 | 0 | 0 | 0 | 0 | 0 |
| 0 | 0 | 1 | 0 | 0 | 1 | 0 | 0 | 1 | 1 | 0 |
| 0 | 0 | 1 | 0 | 1 | 0 | 1 | 0 | 0 | 1 | 1 |
| 0 | 0 | 1 | 0 | 1 | 1 | 0 | 1 | 1 | 1 | 0 |
| 0 | 0 | 1 | 1 | X | X | 1 | 0 | 0 | 1 | 0 |
| 0 | 0 | 1 | 1 | X | X | 1 | 0 | 0 | 1 | 0 |
| 0 | 0 | 1 | 1 | X | X | 1 | 0 | 0 | 1 | 0 |
| 0 | 0 | 1 | 1 | X | X | 1 | 0 | 0 | 1 | 0 |
| 0 | 1 | 0 | 0 | 0 | 0 | 0 | 0 | 0 | 1 | 0 |
| 0 | 1 | 0 | 0 | 0 | 1 | 1 | 0 | 0 | 1 | 1 |
| 0 | 1 | 0 | 0 | 1 | 0 | 0 | 1 | 0 | 1 | 0 |
| 0 | 1 | 0 | 0 | 1 | 1 | 0 | 1 | 1 | 1 | 0 |
| 0 | 1 | 0 | 1 | X | X | 1 | 0 | 0 | 1 | 0 |
| 0 | 1 | 0 | 1 | X | X | 1 | 0 | 0 | 1 | 0 |
| 0 | 1 | 0 | 1 | X | X | 1 | 0 | 0 | 1 | 0 |
| 0 | 1 | 0 | 1 | X | X | 1 | 0 | 0 | 1 | 0 |
| 0 | 1 | 1 | 0 | 0 | 0 | 1 | 0 | 0 | 1 | 1 |
| 0 | 1 | 1 | 0 | 0 | 1 | 0 | 0 | 1 | 1 | 0 |
| 0 | 1 | 1 | 0 | 1 | 0 | 0 | 1 | 0 | 1 | 0 |
| 0 | 1 | 1 | 0 | 1 | 1 | 0 | 1 | 1 | 1 | 0 |
| 0 | 1 | 1 | 1 | X | X | 1 | 0 | 0 | 1 | 0 |
| 0 | 1 | 1 | 1 | X | X | 1 | 0 | 0 | 1 | 0 |
| 0 | 1 | 1 | 1 | X | X | 1 | 0 | 0 | 1 | 0 |
| 1 | 1 | 1 | 1 | X | X | 1 | 0 | 0 | 1 | 0 |
| 1 | 0 | 0 | 0 | 0 | 0 | 1 | 0 | 0 | 1 | 1 |
| 1 | 0 | 0 | 0 | 0 | 1 | 1 | 0 | 0 | 1 | 1 |
| 1 | 0 | 0 | 0 | 1 | 0 | 1 | 0 | 0 | 1 | 1 |
| 1 | 0 | 0 | 0 | 1 | 1 | 1 | 0 | 0 | 1 | 1 |
| 1 | 0 | 0 | 1 | X | X | 1 | 0 | 0 | 1 | 0 |
| 1 | 0 | 0 | 1 | X | X | 1 | 0 | 0 | 1 | 0 |
| 1 | 0 | 0 | 1 | X | X | 1 | 0 | 0 | 1 | 0 |
| 1 | 0 | 0 | 1 | X | X | 1 | 0 | 0 | 1 | 0 |
| 1 | 0 | 1 | 0 | 0 | 0 | 0 | 0 | 0 | 1 | 0 |
| 1 | 0 | 1 | 0 | 0 | 1 | 1 | 0 | 1 | 1 | 0 |
| 1 | 0 | 1 | 0 | 1 | 0 | 1 | 0 | 0 | 1 | 1 |
| 1 | 0 | 1 | 0 | 1 | 1 | 1 | 1 | 1 | 1 | 0 |
| 1 | 0 | 1 | 1 | X | X | 1 | 0 | 0 | 1 | 0 |
| 1 | 0 | 1 | 1 | X | X | 1 | 0 | 0 | 1 | 0 |
| 1 | 0 | 1 | 1 | X | X | 1 | 0 | 0 | 1 | 0 |
| 1 | 0 | 1 | 1 | X | X | 1 | 0 | 0 | 1 | 0 |
| 1 | 1 | 0 | 0 | 0 | 0 | 0 | 0 | 0 | 0 | 0 |
| 1 | 1 | 0 | 0 | 0 | 1 | 1 | 0 | 0 | 1 | 1 |
| 1 | 1 | 0 | 0 | 1 | 0 | 1 | 1 | 0 | 1 | 0 |
| 1 | 1 | 0 | 0 | 1 | 1 | 1 | 1 | 1 | 1 | 0 |
| 1 | 1 | 0 | 1 | X | X | 1 | 0 | 0 | 1 | 0 |
| 1 | 1 | 0 | 1 | X | X | 1 | 0 | 0 | 1 | 0 |
| 1 | 1 | 0 | 1 | X | X | 1 | 0 | 0 | 1 | 0 |
| 1 | 1 | 1 | 0 | 0 | 0 | 1 | 0 | 0 | 1 | 1 |
| 1 | 1 | 1 | 0 | 0 | 1 | 1 | 0 | 1 | 1 | 0 |
| 1 | 1 | 1 | 0 | 1 | 0 | 1 | 1 | 0 | 1 | 0 |
| 1 | 1 | 1 | 0 | 1 | 1 | 1 | 1 | 1 | 1 | 0 |
| 1 | 1 | 1 | 1 | X | X | 1 | 0 | 0 | 1 | 0 |
| 1 | 1 | 1 | 1 | X | X | 1 | 0 | 0 | 1 | 0 |
| 1 | 1 | 1 | 1 | X | X | 1 | 0 | 0 | 1 | 0 |
| 1 | 1 | 1 | 1 | X | X | 1 | 0 | 0 | 1 | 0 |

Glossary A

| Name | Meaning |
|---|---|
| MP2 | master encoder direction output |
| MP1 | internal |
| MP0 | internal |
| SERR | slave error output |
| MDA | master encoder input from first PAL - A line |
| MDB | master encoder input from first PAL - B line |
| MN2 | internal |
| MN1 | internal |
| MN0 | internal |
| MBLIP | master encoder degree count output |
| MERR | master error ouput |
| SP2 | slave encoder direction output |
| SP1 | internal |
| SP0 | internal |
| SDA | internal |
| SDB | internal |
| SN2 | internal |
| SN1 | internal |
| SN0 | internal |
| SBLIP | slave encoder degree count output |

It is preferred that the embodiment of the present invention also include an error detection structure 178 whereby if an illegal logic state occurs, such as if the encoder wheel rotates too quickly thus causing a state to be skipped or if an electrical malfunction occurs, the output from the second PAL 176 becomes "frozen." Freezing the output from the second PAL 176 will cause the value which is displayed to the practitioner to also freeze thus indicating that the displayed value may not be valid.

Still referring to FIG. 5, provided below in Table A is a chart showing the logic states output from the third PAL 180. The third PAL 180 is preferably of the same manufacture and model as the first PAL 174 which was described earlier. In Table A, 0=no degrees, 1=1 degree, i.e., high on the output line until the next clock pulse, CW=clockwise direction, CCW=counter clockwise direction, and *=doesn't matter.

TABLE A

| States input to PAL 180 | | Output from PAL 180 | |
|---|---|---|---|
| Encoder 150 | Encoder 154 | Output in degrees | Direction |
| 0° * | 0° * | 0 | * |
| 1° CW | 0° * | 1 | CW |
| 1° CW | 1° CW | 0 | * |
| 1° CW | 1° CCW | 2 | CW |
| 1° CCW | 0° * | 1 | CCW |
| 1° CCW | 1° CCW | 0 | * |
| 1° CCW | 1° CW | 2 | CCW |
| 0° | 1° CW | 1 | CCW |
| 0° | 1° CCW | 1 | CW |

Table A illustrates all of the logic states for determination of degree movement and direction. For instance, if in Table A CW is listed, the input into PAL 180 designated the "direction line" (not explicitly represented in FIG. 5) is high. Conversely, if in Table A CCW is listed, the input into the third PAL 180 designated the "direction line" is low. If 2 degrees is shown in Table A, the "count line" designated on the third PAL 180 "blips" twice.

Provided below is a logic chart which shows the names assigned to the inputs and the various states of the inputs of the third PAL 180 and the resulting output states with the names assigned to those outputs.

Provided below in Glossary B are the meanings of the names assigned to the inputs and the outputs listed in below:

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 0 | 0 | 0 | 0 | 0 | 0 | 0 | 0 | 0 | 0 | 0 | 0 | 0 | 1 | X |
| 0 | 0 | 0 | 0 | 0 | 0 | 0 | 0 | 1 | 0 | 0 | 0 | 0 | 1 | X |
| 0 | 0 | 0 | 0 | 0 | 0 | 0 | 1 | 0 | 0 | 0 | 0 | 0 | 1 | X |
| 0 | 0 | 0 | 0 | 0 | 0 | 0 | 1 | 1 | 0 | 0 | 0 | 0 | 1 | X |
| 0 | 0 | 0 | 0 | 0 | 0 | 1 | 0 | 0 | 0 | 0 | 0 | 0 | 1 | X |
| 0 | 0 | 0 | 0 | 0 | 0 | 1 | 0 | 1 | 0 | 0 | 0 | 0 | 1 | X |
| 0 | 0 | 0 | 0 | 0 | 0 | 1 | 1 | 0 | 0 | 0 | 0 | 0 | 1 | X |
| 0 | 0 | 0 | 0 | 0 | 0 | 1 | 1 | 1 | 0 | 0 | 0 | 0 | 1 | X |
| 0 | 0 | 0 | 0 | 0 | 1 | 0 | 0 | 0 | 0 | 0 | 0 | 0 | 1 | X |
| 0 | 0 | 0 | 0 | 0 | 1 | 0 | 0 | 1 | 0 | 0 | 0 | 0 | 1 | X |
| 0 | 0 | 0 | 0 | 0 | 1 | 0 | 1 | 0 | 0 | 0 | 0 | 0 | 1 | X |
| 0 | 0 | 0 | 0 | 0 | 1 | 0 | 1 | 1 | 0 | 0 | 0 | 0 | 1 | X |
| 0 | 0 | 0 | 0 | 0 | 1 | 1 | 0 | 0 | 0 | 0 | 0 | 0 | 1 | X |
| 0 | 0 | 0 | 0 | 0 | 1 | 1 | 0 | 1 | 0 | 0 | 0 | 0 | 1 | X |
| 0 | 0 | 0 | 0 | 0 | 1 | 1 | 1 | 0 | 0 | 0 | 0 | 0 | 1 | X |
| 0 | 0 | 0 | 0 | 0 | 1 | 1 | 1 | 1 | 0 | 0 | 0 | 0 | 1 | X |
| 0 | 0 | 0 | 0 | 0 | 1 | 0 | 0 | 0 | 0 | 0 | 0 | 0 | 1 | X |
| 0 | 0 | 0 | 0 | 0 | 1 | 0 | 0 | 0 | 1 | 0 | 0 | 1 | 1 | X |
| 0 | 0 | 0 | 0 | 0 | 1 | 0 | 0 | 1 | 0 | 1 | 0 | 1 | 1 | X |
| 0 | 0 | 0 | 0 | 0 | 1 | 0 | 0 | 1 | 1 | 0 | 0 | 0 | 1 | X |
| 0 | 0 | 0 | 0 | 0 | 1 | 0 | 1 | 0 | 0 | 1 | 1 | 0 | 1 | X |
| 0 | 0 | 0 | 0 | 0 | 1 | 0 | 1 | 0 | 1 | 1 | 1 | 0 | 1 | X |
| 0 | 0 | 0 | 0 | 0 | 1 | 0 | 1 | 1 | 0 | 1 | 1 | 0 | 1 | X |
| 0 | 0 | 0 | 0 | 0 | 1 | 0 | 1 | 1 | 1 | 1 | 1 | 0 | 1 | X |
| 0 | 0 | 0 | 0 | 0 | 1 | 1 | 0 | 0 | 0 | 0 | 1 | 0 | 1 | X |
| 0 | 0 | 0 | 0 | 0 | 1 | 1 | 0 | 0 | 1 | 0 | 1 | 0 | 1 | X |
| 0 | 0 | 0 | 0 | 0 | 1 | 1 | 0 | 1 | 0 | 0 | 1 | 0 | 1 | X |
| 0 | 0 | 0 | 0 | 0 | 1 | 1 | 0 | 1 | 1 | 0 | 1 | 0 | 1 | X |
| 0 | 0 | 0 | 0 | 0 | 1 | 1 | 1 | 0 | 0 | 0 | 0 | 0 | 1 | X |
| 0 | 0 | 0 | 0 | 0 | 1 | 1 | 1 | 0 | 1 | 0 | 0 | 0 | 1 | X |

-continued

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 0 | 0 | 0 | 0 | 0 | 1 | 1 | 1 | 1 | 0 | 0 | 0 | 0 | 1 | X |
| 0 | 0 | 0 | 0 | 0 | 1 | 1 | 1 | 1 | 1 | 0 | 0 | 0 | 1 | X |
| 0 | 0 | 0 | 1 | 0 | 0 | 0 | 0 | 0 | 0 | 0 | 0 | 0 | 1 | X |
| 0 | 0 | 0 | 1 | 0 | 0 | 0 | 0 | 1 | 0 | 0 | 0 | 0 | 1 | X |
| 0 | 0 | 0 | 1 | 0 | 0 | 0 | 1 | 0 | 0 | 0 | 0 | 0 | 1 | X |
| 0 | 0 | 0 | 1 | 0 | 0 | 0 | 1 | 1 | 0 | 0 | 0 | 0 | 1 | X |
| 0 | 0 | 0 | 1 | 0 | 0 | 1 | 0 | 0 | 0 | 0 | 0 | 0 | 1 | X |
| 0 | 0 | 0 | 1 | 0 | 0 | 1 | 0 | 1 | 0 | 0 | 0 | 0 | 1 | X |
| 0 | 0 | 0 | 1 | 0 | 0 | 1 | 1 | 0 | 0 | 0 | 0 | 0 | 1 | X |
| 0 | 0 | 0 | 1 | 0 | 0 | 1 | 1 | 1 | 0 | 0 | 0 | 0 | 1 | X |
| 0 | 0 | 0 | 1 | 0 | 1 | 0 | 0 | 0 | 0 | 0 | 0 | 0 | 1 | X |
| 0 | 0 | 0 | 1 | 0 | 1 | 0 | 0 | 1 | 0 | 0 | 0 | 0 | 1 | X |
| 0 | 0 | 0 | 1 | 0 | 1 | 0 | 1 | 0 | 0 | 0 | 0 | 0 | 1 | X |
| 0 | 0 | 0 | 1 | 0 | 1 | 0 | 1 | 1 | 0 | 0 | 0 | 0 | 1 | X |
| 0 | 0 | 0 | 1 | 0 | 1 | 1 | 0 | 0 | 0 | 0 | 0 | 0 | 1 | X |
| 0 | 0 | 0 | 1 | 0 | 1 | 1 | 0 | 1 | 0 | 0 | 0 | 0 | 1 | X |
| 0 | 0 | 0 | 1 | 0 | 1 | 1 | 1 | 0 | 0 | 0 | 0 | 0 | 1 | X |
| 0 | 0 | 0 | 1 | 0 | 1 | 1 | 1 | 1 | 0 | 0 | 0 | 0 | 1 | X |
| 0 | 0 | 0 | 1 | 1 | 0 | 0 | 0 | 0 | 0 | 0 | 1 | 0 | 0 | 0 |
| 0 | 0 | 0 | 1 | 1 | 0 | 0 | 0 | 1 | 0 | 0 | 1 | 0 | 0 | 0 |
| 0 | 0 | 0 | 1 | 1 | 0 | 0 | 1 | 0 | 0 | 0 | 1 | 0 | 0 | 0 |
| 0 | 0 | 0 | 1 | 1 | 0 | 0 | 1 | 1 | 0 | 0 | 1 | 0 | 0 | 0 |
| 0 | 0 | 0 | 1 | 1 | 0 | 1 | 0 | 0 | 0 | 0 | 1 | 0 | 0 | 0 |
| 0 | 0 | 0 | 1 | 1 | 0 | 1 | 0 | 1 | 0 | 0 | 1 | 0 | 0 | 0 |
| 0 | 0 | 0 | 1 | 1 | 0 | 1 | 1 | 0 | 0 | 0 | 1 | 0 | 0 | 0 |
| 0 | 0 | 0 | 1 | 1 | 0 | 1 | 1 | 1 | 0 | 0 | 1 | 0 | 0 | 0 |
| 0 | 0 | 0 | 1 | 1 | 1 | 0 | 0 | 0 | 0 | 0 | 1 | 0 | 0 | 0 |
| 0 | 0 | 0 | 1 | 1 | 1 | 0 | 0 | 1 | 0 | 0 | 1 | 0 | 0 | 0 |
| 0 | 0 | 0 | 1 | 1 | 1 | 0 | 1 | 0 | 0 | 0 | 1 | 0 | 0 | 0 |
| 0 | 0 | 0 | 1 | 1 | 1 | 0 | 1 | 1 | 0 | 0 | 1 | 0 | 0 | 0 |
| 0 | 0 | 0 | 1 | 1 | 1 | 1 | 0 | 0 | 0 | 0 | 1 | 0 | 0 | 0 |
| 0 | 0 | 0 | 1 | 1 | 1 | 1 | 0 | 1 | 0 | 0 | 1 | 0 | 0 | 0 |
| 0 | 0 | 0 | 1 | 1 | 1 | 1 | 1 | 0 | 0 | 0 | 1 | 0 | 0 | 0 |
| 0 | 0 | 0 | 1 | 1 | 1 | 1 | 1 | 1 | 0 | 0 | 1 | 0 | 0 | 0 |
| 0 | 0 | 1 | 0 | 0 | 0 | 0 | 0 | 0 | 0 | 0 | 0 | 0 | 1 | X |
| 0 | 0 | 1 | 0 | 0 | 0 | 0 | 0 | 1 | 0 | 0 | 0 | 0 | 1 | X |
| 0 | 0 | 1 | 0 | 0 | 0 | 0 | 1 | 0 | 0 | 0 | 0 | 0 | 1 | X |
| 0 | 0 | 1 | 0 | 0 | 0 | 0 | 1 | 1 | 0 | 0 | 0 | 0 | 1 | X |
| 0 | 0 | 1 | 0 | 0 | 0 | 1 | 0 | 0 | 0 | 0 | 0 | 0 | 1 | X |
| 0 | 0 | 1 | 0 | 0 | 0 | 1 | 0 | 1 | 0 | 0 | 0 | 0 | 1 | X |
| 0 | 0 | 1 | 0 | 0 | 0 | 1 | 1 | 0 | 0 | 0 | 0 | 0 | 1 | X |
| 0 | 0 | 1 | 0 | 0 | 0 | 1 | 1 | 1 | 0 | 0 | 0 | 0 | 1 | X |
| 0 | 0 | 1 | 0 | 0 | 1 | 0 | 0 | 0 | 0 | 0 | 0 | 0 | 1 | X |
| 0 | 0 | 1 | 0 | 0 | 1 | 0 | 0 | 1 | 0 | 0 | 0 | 0 | 1 | X |
| 0 | 0 | 1 | 0 | 0 | 1 | 0 | 1 | 0 | 0 | 0 | 0 | 0 | 1 | X |
| 0 | 0 | 1 | 0 | 0 | 1 | 0 | 1 | 1 | 0 | 0 | 0 | 0 | 1 | X |
| 0 | 0 | 1 | 0 | 0 | 1 | 1 | 0 | 0 | 0 | 0 | 0 | 0 | 1 | X |
| 0 | 0 | 1 | 0 | 0 | 1 | 1 | 0 | 1 | 0 | 0 | 0 | 0 | 1 | X |
| 0 | 0 | 1 | 0 | 0 | 1 | 1 | 1 | 0 | 0 | 0 | 0 | 0 | 1 | X |
| 0 | 0 | 1 | 0 | 0 | 1 | 1 | 1 | 1 | 0 | 0 | 0 | 0 | 1 | X |
| 0 | 0 | 1 | 0 | 1 | 0 | 0 | 0 | 0 | 0 | 0 | 1 | 1 | 1 | 0 |
| 0 | 0 | 1 | 0 | 1 | 0 | 0 | 0 | 1 | 0 | 0 | 1 | 1 | 1 | 0 |
| 0 | 0 | 1 | 0 | 1 | 0 | 0 | 1 | 0 | 0 | 0 | 1 | 1 | 1 | 0 |
| 0 | 0 | 1 | 0 | 1 | 0 | 0 | 1 | 1 | 0 | 0 | 1 | 1 | 1 | 0 |
| 0 | 0 | 1 | 0 | 1 | 0 | 1 | 0 | 0 | 0 | 0 | 1 | 1 | 1 | 0 |
| 0 | 0 | 1 | 0 | 1 | 0 | 1 | 0 | 1 | 0 | 0 | 1 | 1 | 1 | 0 |
| 0 | 0 | 1 | 0 | 1 | 0 | 1 | 1 | 0 | 0 | 0 | 1 | 1 | 1 | 0 |
| 0 | 0 | 1 | 0 | 1 | 0 | 1 | 1 | 1 | 0 | 0 | 1 | 1 | 1 | 0 |
| 0 | 0 | 1 | 0 | 1 | 1 | 0 | 0 | 0 | 0 | 0 | 1 | 1 | 1 | 0 |
| 0 | 0 | 1 | 0 | 1 | 1 | 0 | 0 | 1 | 0 | 0 | 1 | 1 | 1 | 0 |
| 0 | 0 | 1 | 0 | 1 | 1 | 0 | 1 | 0 | 0 | 0 | 1 | 1 | 1 | 0 |
| 0 | 0 | 1 | 0 | 1 | 1 | 0 | 1 | 1 | 0 | 0 | 1 | 1 | 1 | 0 |
| 0 | 0 | 1 | 0 | 1 | 1 | 1 | 0 | 0 | 0 | 0 | 1 | 1 | 1 | 0 |
| 0 | 0 | 1 | 0 | 1 | 1 | 1 | 0 | 1 | 0 | 0 | 1 | 1 | 1 | 0 |
| 0 | 0 | 1 | 0 | 1 | 1 | 1 | 1 | 0 | 0 | 0 | 1 | 1 | 1 | 0 |
| 0 | 0 | 1 | 0 | 1 | 1 | 1 | 1 | 1 | 0 | 0 | 1 | 1 | 1 | 0 |
| 0 | 0 | 1 | 1 | 0 | 0 | 0 | 0 | 0 | 0 | 0 | 0 | 0 | 1 | X |
| 0 | 0 | 1 | 1 | 0 | 0 | 0 | 0 | 1 | 0 | 0 | 0 | 0 | 1 | X |
| 0 | 0 | 1 | 1 | 0 | 0 | 0 | 1 | 0 | 0 | 0 | 0 | 0 | 1 | X |
| 0 | 0 | 1 | 1 | 0 | 0 | 0 | 1 | 1 | 0 | 0 | 0 | 0 | 1 | X |
| 0 | 0 | 1 | 1 | 0 | 0 | 1 | 0 | 0 | 0 | 0 | 0 | 0 | 1 | X |
| 0 | 0 | 1 | 1 | 0 | 0 | 1 | 0 | 1 | 0 | 0 | 0 | 0 | 1 | X |
| 0 | 0 | 1 | 1 | 0 | 0 | 1 | 1 | 0 | 0 | 0 | 0 | 0 | 1 | X |
| 0 | 0 | 1 | 1 | 0 | 0 | 1 | 1 | 1 | 0 | 0 | 0 | 0 | 1 | X |
| 0 | 0 | 1 | 1 | 0 | 1 | 0 | 0 | 0 | 0 | 0 | 0 | 0 | 1 | X |
| 0 | 0 | 1 | 1 | 0 | 1 | 0 | 0 | 1 | 0 | 0 | 0 | 0 | 1 | X |
| 0 | 0 | 1 | 1 | 0 | 1 | 0 | 1 | 0 | 0 | 0 | 0 | 0 | 1 | X |

-continued

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 0 | 0 | 1 | 1 | 0 | 1 | 0 | 1 | 1 | 0 | 0 | 0 | 0 | 1 | X |
| 0 | 0 | 1 | 1 | 0 | 1 | 1 | 0 | 0 | 0 | 0 | 0 | 0 | 1 | X |
| 0 | 0 | 1 | 1 | 0 | 1 | 1 | 0 | 1 | 0 | 0 | 0 | 0 | 1 | X |
| 0 | 0 | 1 | 1 | 0 | 1 | 1 | 1 | 0 | 0 | 0 | 0 | 0 | 1 | X |
| 0 | 0 | 1 | 1 | 0 | 1 | 1 | 1 | 1 | 0 | 0 | 0 | 0 | 1 | X |
| 0 | 0 | 1 | 1 | 1 | 0 | 0 | 0 | 0 | 0 | 0 | 0 | 0 | 0 | 0 |
| 0 | 0 | 1 | 1 | 1 | 0 | 0 | 0 | 1 | 0 | 0 | 0 | 0 | 0 | 0 |
| 0 | 0 | 1 | 1 | 1 | 0 | 0 | 1 | 0 | 0 | 0 | 0 | 0 | 0 | 0 |
| 0 | 0 | 1 | 1 | 1 | 0 | 0 | 1 | 1 | 0 | 0 | 0 | 0 | 0 | 0 |
| 0 | 0 | 1 | 1 | 1 | 0 | 1 | 0 | 0 | 0 | 0 | 0 | 0 | 0 | 0 |
| 0 | 0 | 1 | 1 | 1 | 0 | 1 | 0 | 1 | 0 | 0 | 0 | 0 | 0 | 0 |
| 0 | 0 | 1 | 1 | 1 | 0 | 1 | 1 | 0 | 0 | 0 | 0 | 0 | 0 | 0 |
| 0 | 0 | 1 | 1 | 1 | 0 | 1 | 1 | 1 | 0 | 0 | 0 | 0 | 0 | 0 |
| 0 | 0 | 1 | 1 | 1 | 1 | 0 | 0 | 0 | 0 | 0 | 0 | 0 | 0 | 0 |
| 0 | 0 | 1 | 1 | 1 | 1 | 0 | 0 | 1 | 0 | 0 | 0 | 0 | 0 | 0 |
| 0 | 0 | 1 | 1 | 1 | 1 | 0 | 1 | 0 | 0 | 0 | 0 | 0 | 0 | 0 |
| 0 | 0 | 1 | 1 | 1 | 1 | 0 | 1 | 1 | 0 | 0 | 0 | 0 | 0 | 0 |
| 0 | 0 | 1 | 1 | 1 | 1 | 1 | 0 | 0 | 0 | 0 | 0 | 0 | 0 | 0 |
| 0 | 0 | 1 | 1 | 1 | 1 | 1 | 0 | 1 | 0 | 0 | 0 | 0 | 0 | 0 |
| 0 | 0 | 1 | 1 | 1 | 1 | 1 | 1 | 0 | 0 | 0 | 0 | 0 | 0 | 0 |
| 0 | 0 | 1 | 1 | 1 | 1 | 1 | 1 | 1 | 0 | 0 | 0 | 0 | 0 | 0 |
| 0 | 1 | 0 | 0 | 0 | 0 | 0 | 0 | 0 | 0 | 0 | 0 | 0 | 1 | X |
| 0 | 1 | 0 | 0 | 0 | 0 | 0 | 0 | 1 | 0 | 0 | 0 | 0 | 1 | X |
| 0 | 1 | 0 | 0 | 0 | 0 | 0 | 1 | 0 | 0 | 0 | 0 | 0 | 1 | X |
| 0 | 1 | 0 | 0 | 0 | 0 | 0 | 1 | 1 | 0 | 0 | 0 | 0 | 1 | X |
| 0 | 1 | 0 | 0 | 0 | 0 | 1 | 0 | 0 | 0 | 0 | 0 | 0 | 1 | X |
| 0 | 1 | 0 | 0 | 0 | 0 | 1 | 0 | 1 | 0 | 0 | 0 | 0 | 1 | X |
| 0 | 1 | 0 | 0 | 0 | 0 | 1 | 1 | 0 | 0 | 0 | 0 | 0 | 1 | X |
| 0 | 1 | 0 | 0 | 0 | 0 | 1 | 1 | 1 | 0 | 0 | 0 | 0 | 1 | X |
| 0 | 1 | 0 | 0 | 0 | 1 | 0 | 0 | 0 | 0 | 0 | 0 | 0 | 1 | X |
| 0 | 1 | 0 | 0 | 0 | 1 | 0 | 0 | 1 | 0 | 0 | 0 | 0 | 1 | X |
| 0 | 1 | 0 | 0 | 0 | 1 | 0 | 1 | 0 | 0 | 0 | 0 | 0 | 1 | X |
| 0 | 1 | 0 | 0 | 0 | 1 | 0 | 1 | 1 | 0 | 0 | 0 | 0 | 1 | X |
| 0 | 1 | 0 | 0 | 0 | 1 | 1 | 0 | 0 | 0 | 0 | 0 | 0 | 1 | X |
| 0 | 1 | 0 | 0 | 0 | 1 | 1 | 0 | 1 | 0 | 0 | 0 | 0 | 1 | X |
| 0 | 1 | 0 | 0 | 0 | 1 | 1 | 1 | 0 | 0 | 0 | 0 | 0 | 1 | X |
| 0 | 1 | 0 | 0 | 0 | 1 | 1 | 1 | 1 | 0 | 0 | 0 | 0 | 1 | X |
| 0 | 1 | 0 | 0 | 1 | 0 | 0 | 0 | 0 | 0 | 1 | 1 | 1 | 0 | 1 |
| 0 | 1 | 0 | 0 | 1 | 0 | 0 | 0 | 1 | 0 | 1 | 1 | 1 | 0 | 1 |
| 0 | 1 | 0 | 0 | 1 | 0 | 0 | 1 | 0 | 0 | 1 | 0 | 1 | 0 | 1 |
| 0 | 1 | 0 | 0 | 1 | 0 | 0 | 1 | 1 | 0 | 1 | 0 | 1 | 0 | 1 |
| 0 | 1 | 0 | 0 | 1 | 0 | 1 | 0 | 0 | 0 | 1 | 1 | 1 | 0 | 1 |
| 0 | 1 | 0 | 0 | 1 | 0 | 1 | 0 | 1 | 0 | 1 | 1 | 1 | 0 | 1 |
| 0 | 1 | 0 | 0 | 1 | 0 | 1 | 1 | 0 | 0 | 1 | 0 | 1 | 0 | 1 |
| 0 | 1 | 0 | 0 | 1 | 0 | 1 | 1 | 1 | 0 | 1 | 0 | 1 | 0 | 1 |
| 0 | 1 | 0 | 0 | 1 | 1 | 0 | 0 | 0 | 0 | 0 | 0 | 0 | 0 | 1 |
| 0 | 1 | 0 | 0 | 1 | 1 | 0 | 0 | 1 | 0 | 0 | 0 | 0 | 0 | 1 |
| 0 | 1 | 0 | 0 | 1 | 1 | 0 | 1 | 0 | 0 | 0 | 0 | 0 | 0 | 1 |
| 0 | 1 | 0 | 0 | 1 | 1 | 0 | 1 | 1 | 0 | 0 | 0 | 0 | 0 | 1 |
| 0 | 1 | 0 | 0 | 1 | 1 | 1 | 0 | 0 | 0 | 0 | 0 | 0 | 0 | 1 |
| 0 | 1 | 0 | 0 | 1 | 1 | 1 | 0 | 1 | 0 | 0 | 0 | 0 | 0 | 1 |
| 0 | 1 | 0 | 0 | 1 | 1 | 1 | 1 | 0 | 0 | 0 | 0 | 0 | 0 | 1 |
| 0 | 1 | 0 | 0 | 1 | 1 | 1 | 1 | 1 | 0 | 0 | 0 | 0 | 0 | 1 |
| 0 | 1 | 0 | 1 | 0 | 0 | 0 | 0 | 0 | 0 | 0 | 0 | 0 | 1 | X |
| 0 | 1 | 0 | 1 | 0 | 0 | 0 | 0 | 1 | 0 | 0 | 0 | 0 | 1 | X |
| 0 | 1 | 0 | 1 | 0 | 0 | 0 | 1 | 0 | 0 | 0 | 0 | 0 | 1 | X |
| 0 | 1 | 0 | 1 | 0 | 0 | 0 | 1 | 1 | 0 | 0 | 0 | 0 | 1 | X |
| 0 | 1 | 0 | 1 | 0 | 0 | 1 | 0 | 0 | 0 | 0 | 0 | 0 | 1 | X |
| 0 | 1 | 0 | 1 | 0 | 0 | 1 | 0 | 1 | 0 | 0 | 0 | 0 | 1 | X |
| 0 | 1 | 0 | 1 | 0 | 0 | 1 | 1 | 0 | 0 | 0 | 0 | 0 | 1 | X |
| 0 | 1 | 0 | 1 | 0 | 0 | 1 | 1 | 1 | 0 | 0 | 0 | 0 | 1 | X |
| 0 | 1 | 0 | 1 | 0 | 1 | 0 | 0 | 0 | 0 | 0 | 0 | 0 | 1 | X |
| 0 | 1 | 0 | 1 | 0 | 1 | 0 | 0 | 1 | 0 | 0 | 0 | 0 | 1 | X |
| 0 | 1 | 0 | 1 | 0 | 1 | 0 | 1 | 0 | 0 | 0 | 0 | 0 | 1 | X |
| 0 | 1 | 0 | 1 | 0 | 1 | 0 | 1 | 1 | 0 | 0 | 0 | 0 | 1 | X |
| 0 | 1 | 0 | 1 | 0 | 1 | 1 | 0 | 0 | 0 | 0 | 0 | 0 | 1 | X |
| 0 | 1 | 0 | 1 | 0 | 1 | 1 | 0 | 1 | 0 | 0 | 0 | 0 | 1 | X |
| 0 | 1 | 0 | 1 | 0 | 1 | 1 | 1 | 0 | 0 | 0 | 0 | 0 | 1 | X |
| 0 | 1 | 0 | 1 | 0 | 1 | 1 | 1 | 1 | 0 | 0 | 0 | 0 | 1 | X |
| 0 | 1 | 0 | 1 | 1 | 0 | 0 | 0 | 0 | 1 | 1 | 0 | 0 | 1 | X |
| 0 | 1 | 0 | 1 | 1 | 0 | 0 | 0 | 1 | 1 | 1 | 0 | 0 | 1 | X |
| 0 | 1 | 0 | 1 | 1 | 0 | 0 | 1 | 0 | 1 | 1 | 0 | 0 | 1 | X |
| 0 | 1 | 0 | 1 | 1 | 0 | 0 | 1 | 1 | 1 | 1 | 0 | 0 | 1 | X |
| 0 | 1 | 0 | 1 | 1 | 0 | 1 | 0 | 0 | 1 | 1 | 0 | 0 | 1 | X |
| 0 | 1 | 0 | 1 | 1 | 0 | 1 | 0 | 1 | 1 | 1 | 0 | 0 | 1 | X |
| 0 | 1 | 0 | 1 | 1 | 0 | 1 | 1 | 0 | 1 | 1 | 0 | 0 | 1 | X |
| 0 | 1 | 0 | 1 | 1 | 0 | 1 | 1 | 1 | 1 | 1 | 0 | 0 | 1 | X |

-continued

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 0 | 1 | 0 | 1 | 1 | 1 | 0 | 0 | 0 | 1 | 1 | 0 | 0 | 1 | X |
| 0 | 1 | 0 | 1 | 1 | 1 | 0 | 0 | 1 | 1 | 1 | 0 | 0 | 1 | X |
| 0 | 1 | 0 | 1 | 1 | 1 | 0 | 1 | 0 | 1 | 1 | 0 | 0 | 1 | X |
| 0 | 1 | 0 | 1 | 1 | 1 | 0 | 1 | 1 | 1 | 1 | 0 | 0 | 1 | X |
| 0 | 1 | 0 | 1 | 1 | 1 | 1 | 0 | 0 | 1 | 1 | 0 | 0 | 1 | X |
| 0 | 1 | 0 | 1 | 1 | 1 | 1 | 0 | 1 | 1 | 1 | 0 | 0 | 1 | X |
| 0 | 1 | 0 | 1 | 1 | 1 | 1 | 1 | 0 | 1 | 1 | 0 | 0 | 1 | X |
| 0 | 1 | 0 | 1 | 1 | 1 | 1 | 1 | 1 | 1 | 1 | 0 | 0 | 1 | X |
| 0 | 1 | 1 | 0 | 0 | 0 | 0 | 0 | 0 | 0 | 0 | 0 | 0 | 1 | X |
| 0 | 1 | 1 | 0 | 0 | 0 | 0 | 0 | 1 | 0 | 0 | 0 | 0 | 1 | X |
| 0 | 1 | 1 | 0 | 0 | 0 | 0 | 1 | 0 | 0 | 0 | 0 | 0 | 1 | X |
| 0 | 1 | 1 | 0 | 0 | 0 | 0 | 1 | 1 | 0 | 0 | 0 | 0 | 1 | X |
| 0 | 1 | 1 | 0 | 0 | 0 | 1 | 0 | 0 | 0 | 0 | 0 | 0 | 1 | X |
| 0 | 1 | 1 | 0 | 0 | 0 | 1 | 0 | 1 | 0 | 0 | 0 | 0 | 1 | X |
| 0 | 1 | 1 | 0 | 0 | 0 | 1 | 1 | 0 | 0 | 0 | 0 | 0 | 1 | X |
| 0 | 1 | 1 | 0 | 0 | 0 | 1 | 1 | 1 | 0 | 0 | 0 | 0 | 1 | X |
| 0 | 1 | 1 | 0 | 0 | 1 | 0 | 0 | 0 | 0 | 0 | 0 | 0 | 1 | X |
| 0 | 1 | 1 | 0 | 0 | 1 | 0 | 0 | 1 | 0 | 0 | 0 | 0 | 1 | X |
| 0 | 1 | 1 | 0 | 0 | 1 | 0 | 1 | 0 | 0 | 0 | 0 | 0 | 1 | X |
| 0 | 1 | 1 | 0 | 0 | 1 | 0 | 1 | 1 | 0 | 0 | 0 | 0 | 1 | X |
| 0 | 1 | 1 | 0 | 0 | 1 | 1 | 0 | 0 | 0 | 0 | 0 | 0 | 1 | X |
| 0 | 1 | 1 | 0 | 0 | 1 | 1 | 0 | 1 | 0 | 0 | 0 | 0 | 1 | X |
| 0 | 1 | 1 | 0 | 0 | 1 | 1 | 1 | 0 | 0 | 0 | 0 | 0 | 1 | X |
| 0 | 1 | 1 | 0 | 0 | 1 | 1 | 1 | 1 | 0 | 0 | 0 | 0 | 1 | X |
| 0 | 1 | 1 | 0 | 1 | 0 | 0 | 0 | 0 | 0 | 1 | 1 | 1 | 0 | 0 |
| 0 | 1 | 1 | 0 | 1 | 0 | 0 | 0 | 1 | 0 | 1 | 1 | 1 | 0 | 0 |
| 0 | 1 | 1 | 0 | 1 | 0 | 0 | 1 | 0 | 0 | 1 | 0 | 1 | 0 | 0 |
| 0 | 1 | 1 | 0 | 1 | 0 | 0 | 1 | 1 | 0 | 1 | 0 | 1 | 0 | 0 |
| 0 | 1 | 1 | 0 | 1 | 0 | 1 | 0 | 0 | 0 | 1 | 1 | 1 | 0 | 0 |
| 0 | 1 | 1 | 0 | 1 | 0 | 1 | 0 | 1 | 0 | 1 | 1 | 1 | 0 | 0 |
| 0 | 1 | 1 | 0 | 1 | 0 | 1 | 1 | 0 | 0 | 1 | 0 | 1 | 0 | 0 |
| 0 | 1 | 1 | 0 | 1 | 0 | 1 | 1 | 1 | 0 | 1 | 0 | 1 | 0 | 0 |
| 0 | 1 | 1 | 0 | 1 | 1 | 0 | 0 | 0 | 0 | 0 | 0 | 0 | 0 | 0 |
| 0 | 1 | 1 | 0 | 1 | 1 | 0 | 0 | 1 | 0 | 0 | 0 | 0 | 0 | 0 |
| 0 | 1 | 1 | 0 | 1 | 1 | 0 | 1 | 0 | 0 | 0 | 0 | 0 | 0 | 0 |
| 0 | 1 | 1 | 0 | 1 | 1 | 0 | 1 | 1 | 0 | 0 | 0 | 0 | 0 | 0 |
| 0 | 1 | 1 | 0 | 1 | 1 | 1 | 0 | 0 | 0 | 0 | 0 | 0 | 0 | 0 |
| 0 | 1 | 1 | 0 | 1 | 1 | 1 | 0 | 1 | 0 | 0 | 0 | 0 | 0 | 0 |
| 0 | 1 | 1 | 0 | 1 | 1 | 1 | 1 | 0 | 0 | 0 | 0 | 0 | 0 | 0 |
| 0 | 1 | 1 | 0 | 1 | 1 | 1 | 1 | 1 | 0 | 0 | 0 | 0 | 0 | 0 |
| 0 | 1 | 1 | 1 | 0 | 0 | 0 | 0 | 0 | 0 | 0 | 0 | 0 | 1 | X |
| 0 | 1 | 1 | 1 | 0 | 0 | 0 | 0 | 1 | 0 | 0 | 0 | 0 | 1 | X |
| 0 | 1 | 1 | 1 | 0 | 0 | 0 | 1 | 0 | 0 | 0 | 0 | 0 | 1 | X |
| 0 | 1 | 1 | 1 | 0 | 0 | 0 | 1 | 1 | 0 | 0 | 0 | 0 | 1 | X |
| 0 | 1 | 1 | 1 | 0 | 0 | 1 | 0 | 0 | 0 | 0 | 0 | 0 | 1 | X |
| 0 | 1 | 1 | 1 | 0 | 0 | 1 | 0 | 1 | 0 | 0 | 0 | 0 | 1 | X |
| 0 | 1 | 1 | 1 | 0 | 0 | 1 | 1 | 0 | 0 | 0 | 0 | 0 | 1 | X |
| 0 | 1 | 1 | 1 | 0 | 0 | 1 | 1 | 1 | 0 | 0 | 0 | 0 | 1 | X |
| 0 | 1 | 1 | 1 | 0 | 1 | 0 | 0 | 0 | 0 | 0 | 0 | 0 | 1 | X |
| 0 | 1 | 1 | 1 | 0 | 1 | 0 | 0 | 1 | 0 | 0 | 0 | 0 | 1 | X |
| 0 | 1 | 1 | 1 | 0 | 1 | 0 | 1 | 0 | 0 | 0 | 0 | 0 | 1 | X |
| 0 | 1 | 1 | 1 | 0 | 1 | 0 | 1 | 1 | 0 | 0 | 0 | 0 | 1 | X |
| 0 | 1 | 1 | 1 | 0 | 1 | 1 | 0 | 0 | 0 | 0 | 0 | 0 | 1 | X |
| 0 | 1 | 1 | 1 | 0 | 1 | 1 | 0 | 1 | 0 | 0 | 0 | 0 | 1 | X |
| 0 | 1 | 1 | 1 | 0 | 1 | 1 | 1 | 0 | 0 | 0 | 0 | 0 | 1 | X |
| 0 | 1 | 1 | 1 | 0 | 1 | 1 | 1 | 1 | 0 | 0 | 0 | 0 | 1 | X |
| 1 | 0 | 0 | 1 | 0 | 0 | 0 | 0 | 0 | 0 | 0 | 0 | 0 | 1 | X |
| 1 | 0 | 0 | 1 | 0 | 0 | 0 | 0 | 1 | 0 | 0 | 0 | 0 | 1 | X |
| 1 | 0 | 0 | 1 | 0 | 0 | 0 | 1 | 0 | 0 | 0 | 0 | 0 | 1 | X |
| 1 | 0 | 0 | 1 | 0 | 0 | 0 | 1 | 1 | 0 | 0 | 0 | 0 | 1 | X |
| 1 | 0 | 0 | 1 | 0 | 0 | 1 | 0 | 0 | 0 | 0 | 0 | 0 | 1 | X |
| 1 | 0 | 0 | 1 | 0 | 0 | 1 | 0 | 1 | 0 | 0 | 0 | 0 | 1 | X |
| 1 | 0 | 0 | 1 | 0 | 0 | 1 | 1 | 0 | 0 | 0 | 0 | 0 | 1 | X |
| 1 | 0 | 0 | 1 | 0 | 0 | 1 | 1 | 1 | 0 | 0 | 0 | 0 | 1 | X |
| 1 | 0 | 0 | 1 | 0 | 1 | 0 | 0 | 0 | 0 | 0 | 0 | 0 | 1 | X |
| 1 | 0 | 0 | 1 | 0 | 1 | 0 | 0 | 1 | 0 | 0 | 0 | 0 | 1 | X |
| 1 | 0 | 0 | 1 | 0 | 1 | 0 | 1 | 0 | 0 | 0 | 0 | 0 | 1 | X |
| 1 | 0 | 0 | 1 | 0 | 1 | 0 | 1 | 1 | 0 | 0 | 0 | 0 | 1 | X |
| 1 | 0 | 0 | 1 | 0 | 1 | 1 | 0 | 0 | 0 | 0 | 0 | 0 | 1 | X |
| 1 | 0 | 0 | 1 | 0 | 1 | 1 | 0 | 1 | 0 | 0 | 0 | 0 | 1 | X |
| 1 | 0 | 0 | 1 | 0 | 1 | 1 | 1 | 0 | 0 | 0 | 0 | 0 | 1 | X |
| 1 | 0 | 0 | 1 | 0 | 1 | 1 | 1 | 1 | 0 | 0 | 0 | 0 | 1 | X |
| 1 | 0 | 0 | 1 | 1 | 0 | 0 | 0 | 0 | 1 | 0 | 1 | 0 | 0 | 1 |
| 1 | 0 | 0 | 1 | 1 | 0 | 0 | 0 | 1 | 1 | 0 | 1 | 0 | 0 | 1 |
| 1 | 0 | 0 | 1 | 1 | 0 | 0 | 1 | 0 | 1 | 0 | 1 | 0 | 0 | 1 |
| 1 | 0 | 0 | 1 | 1 | 0 | 0 | 1 | 1 | 1 | 0 | 1 | 0 | 0 | 1 |
| 1 | 0 | 0 | 1 | 1 | 0 | 1 | 0 | 0 | 1 | 0 | 1 | 0 | 0 | 1 |

-continued

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 1 | 0 | 0 | 1 | 1 | 0 | 1 | 0 | 1 | 1 | 0 | 1 | 0 | 0 | 1 |
| 1 | 0 | 0 | 1 | 1 | 0 | 1 | 1 | 0 | 1 | 0 | 1 | 0 | 0 | 1 |
| 1 | 0 | 0 | 1 | 1 | 0 | 1 | 1 | 1 | 1 | 0 | 1 | 0 | 0 | 1 |
| 1 | 0 | 0 | 1 | 1 | 1 | 0 | 0 | 0 | 1 | 0 | 1 | 0 | 0 | 1 |
| 1 | 0 | 0 | 1 | 1 | 1 | 0 | 0 | 1 | 1 | 0 | 1 | 0 | 0 | 1 |
| 1 | 0 | 0 | 1 | 1 | 1 | 0 | 1 | 0 | 1 | 0 | 1 | 0 | 0 | 1 |
| 1 | 0 | 0 | 1 | 1 | 1 | 0 | 1 | 1 | 1 | 0 | 1 | 0 | 0 | 1 |
| 1 | 0 | 0 | 1 | 1 | 1 | 1 | 0 | 0 | 1 | 0 | 1 | 0 | 0 | 1 |
| 1 | 0 | 0 | 1 | 1 | 1 | 1 | 0 | 1 | 1 | 0 | 1 | 0 | 0 | 1 |
| 1 | 0 | 0 | 1 | 1 | 1 | 1 | 1 | 0 | 1 | 0 | 1 | 0 | 0 | 1 |
| 1 | 0 | 0 | 1 | 1 | 1 | 1 | 1 | 1 | 1 | 0 | 1 | 0 | 0 | 1 |
| 1 | 0 | 1 | 0 | 0 | 0 | 0 | 0 | 0 | 0 | 0 | 0 | 0 | 1 | X |
| 1 | 0 | 1 | 0 | 0 | 0 | 0 | 0 | 1 | 0 | 0 | 0 | 0 | 1 | X |
| 1 | 0 | 1 | 0 | 0 | 0 | 0 | 1 | 0 | 0 | 0 | 0 | 0 | 1 | X |
| 1 | 0 | 1 | 0 | 0 | 0 | 0 | 1 | 1 | 0 | 0 | 0 | 0 | 1 | X |
| 1 | 0 | 1 | 0 | 0 | 0 | 1 | 0 | 0 | 0 | 0 | 0 | 0 | 1 | X |
| 1 | 0 | 1 | 0 | 0 | 0 | 1 | 0 | 1 | 0 | 0 | 0 | 0 | 1 | X |
| 1 | 0 | 1 | 0 | 0 | 0 | 1 | 1 | 0 | 0 | 0 | 0 | 0 | 1 | X |
| 1 | 0 | 1 | 0 | 0 | 0 | 1 | 1 | 1 | 0 | 0 | 0 | 0 | 1 | X |
| 1 | 0 | 1 | 0 | 0 | 1 | 0 | 0 | 0 | 0 | 0 | 0 | 0 | 1 | X |
| 1 | 0 | 1 | 0 | 0 | 1 | 0 | 0 | 1 | 0 | 0 | 0 | 0 | 1 | X |
| 1 | 0 | 1 | 0 | 0 | 1 | 0 | 1 | 0 | 0 | 0 | 0 | 0 | 1 | X |
| 1 | 0 | 1 | 0 | 0 | 1 | 0 | 1 | 1 | 0 | 0 | 0 | 0 | 1 | X |
| 1 | 0 | 1 | 0 | 0 | 1 | 1 | 0 | 0 | 0 | 0 | 0 | 0 | 1 | X |
| 1 | 0 | 1 | 0 | 0 | 1 | 1 | 0 | 1 | 0 | 0 | 0 | 0 | 1 | X |
| 1 | 0 | 1 | 0 | 0 | 1 | 1 | 1 | 0 | 0 | 0 | 0 | 0 | 1 | X |
| 1 | 0 | 1 | 0 | 0 | 1 | 1 | 1 | 1 | 0 | 0 | 0 | 0 | 1 | X |
| 1 | 0 | 1 | 0 | 1 | 0 | 0 | 0 | 0 | 1 | 0 | 1 | 1 | 1 | 1 |
| 1 | 0 | 1 | 0 | 1 | 0 | 0 | 0 | 1 | 1 | 0 | 1 | 1 | 1 | 1 |
| 1 | 0 | 1 | 0 | 1 | 0 | 0 | 1 | 0 | 1 | 0 | 1 | 1 | 1 | 1 |
| 1 | 0 | 1 | 0 | 1 | 0 | 0 | 1 | 1 | 1 | 0 | 1 | 1 | 1 | 1 |
| 1 | 0 | 1 | 0 | 1 | 0 | 1 | 0 | 0 | 1 | 0 | 1 | 1 | 1 | 1 |
| 1 | 0 | 1 | 0 | 1 | 0 | 1 | 0 | 1 | 1 | 0 | 1 | 1 | 1 | 1 |
| 1 | 0 | 1 | 0 | 1 | 0 | 1 | 1 | 0 | 1 | 0 | 1 | 1 | 1 | 1 |
| 1 | 0 | 1 | 0 | 1 | 0 | 1 | 1 | 1 | 1 | 0 | 1 | 1 | 1 | 1 |
| 1 | 0 | 1 | 0 | 1 | 1 | 0 | 0 | 0 | 1 | 0 | 1 | 1 | 1 | 1 |
| 1 | 0 | 1 | 0 | 1 | 1 | 0 | 0 | 1 | 1 | 0 | 1 | 1 | 1 | 1 |
| 1 | 0 | 1 | 0 | 1 | 1 | 0 | 1 | 0 | 1 | 0 | 1 | 1 | 1 | 1 |
| 1 | 0 | 1 | 0 | 1 | 1 | 0 | 1 | 1 | 1 | 0 | 1 | 1 | 1 | 1 |
| 1 | 0 | 1 | 0 | 1 | 1 | 1 | 0 | 0 | 1 | 0 | 1 | 1 | 1 | 1 |
| 1 | 0 | 1 | 0 | 1 | 1 | 1 | 0 | 1 | 1 | 0 | 1 | 1 | 1 | 1 |
| 1 | 0 | 1 | 0 | 1 | 1 | 1 | 1 | 0 | 1 | 0 | 1 | 1 | 1 | 1 |
| 1 | 0 | 1 | 0 | 1 | 1 | 1 | 1 | 1 | 1 | 0 | 1 | 1 | 1 | 1 |
| 1 | 0 | 1 | 1 | 0 | 0 | 0 | 0 | 0 | 0 | 0 | 0 | 0 | 1 | X |
| 1 | 0 | 1 | 1 | 0 | 0 | 0 | 0 | 1 | 0 | 0 | 0 | 0 | 1 | X |
| 1 | 0 | 1 | 1 | 0 | 0 | 0 | 1 | 0 | 0 | 0 | 0 | 0 | 1 | X |
| 1 | 0 | 1 | 1 | 0 | 0 | 0 | 1 | 1 | 0 | 0 | 0 | 0 | 1 | X |
| 1 | 0 | 1 | 1 | 0 | 0 | 1 | 0 | 0 | 0 | 0 | 0 | 0 | 1 | X |
| 1 | 0 | 1 | 1 | 0 | 0 | 1 | 0 | 1 | 0 | 0 | 0 | 0 | 1 | X |
| 1 | 0 | 1 | 1 | 0 | 0 | 1 | 1 | 0 | 0 | 0 | 0 | 0 | 1 | X |
| 1 | 0 | 1 | 1 | 0 | 0 | 1 | 1 | 1 | 0 | 0 | 0 | 0 | 1 | X |
| 1 | 0 | 1 | 1 | 0 | 1 | 0 | 0 | 0 | 0 | 0 | 0 | 0 | 1 | X |
| 1 | 0 | 1 | 1 | 0 | 1 | 0 | 0 | 1 | 0 | 0 | 0 | 0 | 1 | X |
| 1 | 0 | 1 | 1 | 0 | 1 | 0 | 1 | 0 | 0 | 0 | 0 | 0 | 1 | X |
| 1 | 0 | 1 | 1 | 0 | 1 | 0 | 1 | 1 | 0 | 0 | 0 | 0 | 1 | X |
| 1 | 0 | 1 | 1 | 0 | 1 | 1 | 0 | 0 | 0 | 0 | 0 | 0 | 1 | X |
| 1 | 0 | 1 | 1 | 0 | 1 | 1 | 0 | 1 | 0 | 0 | 0 | 0 | 1 | X |
| 1 | 0 | 1 | 1 | 0 | 1 | 1 | 1 | 0 | 0 | 0 | 0 | 0 | 1 | X |
| 1 | 0 | 1 | 1 | 0 | 1 | 1 | 1 | 1 | 0 | 0 | 0 | 0 | 1 | X |
| 1 | 0 | 1 | 1 | 1 | 0 | 0 | 0 | 0 | 0 | 0 | 0 | 0 | 0 | 1 |
| 1 | 0 | 1 | 1 | 1 | 0 | 0 | 0 | 1 | 0 | 0 | 0 | 0 | 0 | 1 |
| 1 | 0 | 1 | 1 | 1 | 0 | 0 | 1 | 0 | 0 | 0 | 0 | 0 | 0 | 1 |
| 1 | 0 | 1 | 1 | 1 | 0 | 0 | 1 | 1 | 0 | 0 | 0 | 0 | 0 | 1 |
| 1 | 0 | 1 | 1 | 1 | 0 | 1 | 0 | 0 | 0 | 0 | 0 | 0 | 0 | 1 |
| 1 | 0 | 1 | 1 | 1 | 0 | 1 | 0 | 1 | 0 | 0 | 0 | 0 | 0 | 1 |
| 1 | 0 | 1 | 1 | 1 | 0 | 1 | 1 | 0 | 0 | 0 | 0 | 0 | 0 | 1 |
| 1 | 0 | 1 | 1 | 1 | 0 | 1 | 1 | 1 | 0 | 0 | 0 | 0 | 0 | 1 |
| 1 | 0 | 1 | 1 | 1 | 1 | 0 | 0 | 0 | 0 | 0 | 0 | 0 | 0 | 1 |
| 1 | 0 | 1 | 1 | 1 | 1 | 0 | 0 | 1 | 0 | 0 | 0 | 0 | 0 | 1 |
| 1 | 0 | 1 | 1 | 1 | 1 | 0 | 1 | 0 | 0 | 0 | 0 | 0 | 0 | 1 |
| 1 | 0 | 1 | 1 | 1 | 1 | 0 | 1 | 1 | 0 | 0 | 0 | 0 | 0 | 1 |
| 1 | 0 | 1 | 1 | 1 | 1 | 1 | 0 | 0 | 0 | 0 | 0 | 0 | 0 | 1 |
| 1 | 0 | 1 | 1 | 1 | 1 | 1 | 0 | 1 | 0 | 0 | 0 | 0 | 0 | 1 |
| 1 | 0 | 1 | 1 | 1 | 1 | 1 | 1 | 0 | 0 | 0 | 0 | 0 | 0 | 1 |
| 1 | 0 | 1 | 1 | 1 | 1 | 1 | 1 | 1 | 0 | 0 | 0 | 0 | 0 | 1 |
| 1 | 1 | 0 | 0 | 0 | 0 | 0 | 0 | 0 | 0 | 0 | 0 | 0 | 1 | X |
| 1 | 1 | 0 | 0 | 0 | 0 | 0 | 0 | 1 | 0 | 0 | 0 | 0 | 1 | X |

-continued

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 1 | 1 | 0 | 0 | 0 | 0 | 0 | 1 | 0 | 0 | 0 | 0 | 0 | 1 | X |
| 1 | 1 | 0 | 0 | 0 | 0 | 0 | 1 | 1 | 0 | 0 | 0 | 0 | 1 | X |
| 1 | 1 | 0 | 0 | 0 | 0 | 1 | 0 | 0 | 0 | 0 | 0 | 0 | 1 | X |
| 1 | 1 | 0 | 0 | 0 | 0 | 1 | 0 | 1 | 0 | 0 | 0 | 0 | 1 | X |
| 1 | 1 | 0 | 0 | 0 | 0 | 1 | 1 | 0 | 0 | 0 | 0 | 0 | 1 | X |
| 1 | 1 | 0 | 0 | 0 | 0 | 1 | 1 | 1 | 0 | 0 | 0 | 0 | 1 | X |
| 1 | 1 | 0 | 0 | 0 | 1 | 0 | 0 | 0 | 0 | 0 | 0 | 0 | 1 | X |
| 1 | 1 | 0 | 0 | 0 | 1 | 0 | 0 | 1 | 0 | 0 | 0 | 0 | 1 | X |
| 1 | 1 | 0 | 0 | 0 | 1 | 0 | 1 | 0 | 0 | 0 | 0 | 0 | 1 | X |
| 1 | 1 | 0 | 0 | 0 | 1 | 0 | 1 | 1 | 0 | 0 | 0 | 0 | 1 | X |
| 1 | 1 | 0 | 0 | 0 | 1 | 1 | 0 | 0 | 0 | 0 | 0 | 0 | 1 | X |
| 1 | 1 | 0 | 0 | 0 | 1 | 1 | 0 | 1 | 0 | 0 | 0 | 0 | 1 | X |
| 1 | 1 | 0 | 0 | 0 | 1 | 1 | 1 | 0 | 0 | 0 | 0 | 0 | 1 | X |
| 1 | 1 | 0 | 0 | 0 | 1 | 1 | 1 | 1 | 0 | 0 | 0 | 0 | 1 | X |
| 1 | 1 | 0 | 0 | 1 | 0 | 0 | 0 | 0 | 1 | 1 | 1 | 1 | 0 | 1 |
| 1 | 1 | 0 | 0 | 1 | 0 | 0 | 0 | 1 | 1 | 1 | 0 | 1 | 0 | 1 |
| 1 | 1 | 0 | 0 | 1 | 0 | 0 | 1 | 0 | 1 | 1 | 1 | 1 | 0 | 1 |
| 1 | 1 | 0 | 0 | 1 | 0 | 0 | 1 | 1 | 1 | 1 | 0 | 1 | 0 | 1 |
| 1 | 1 | 0 | 0 | 1 | 0 | 1 | 0 | 0 | 0 | 0 | 0 | 0 | 0 | 1 |
| 1 | 1 | 0 | 0 | 1 | 0 | 1 | 0 | 1 | 0 | 0 | 0 | 0 | 0 | 1 |
| 1 | 1 | 0 | 0 | 1 | 0 | 1 | 1 | 0 | 0 | 0 | 0 | 0 | 0 | 1 |
| 1 | 1 | 0 | 0 | 1 | 0 | 1 | 1 | 1 | 0 | 0 | 0 | 0 | 0 | 1 |
| 1 | 1 | 0 | 0 | 1 | 1 | 0 | 0 | 0 | 1 | 1 | 1 | 1 | 0 | 1 |
| 1 | 1 | 0 | 0 | 1 | 1 | 0 | 0 | 1 | 1 | 1 | 0 | 1 | 0 | 1 |
| 1 | 1 | 0 | 0 | 1 | 1 | 0 | 1 | 0 | 1 | 1 | 1 | 1 | 0 | 1 |
| 1 | 1 | 0 | 0 | 1 | 1 | 0 | 1 | 1 | 1 | 1 | 0 | 1 | 0 | 1 |
| 1 | 1 | 0 | 0 | 1 | 1 | 1 | 0 | 0 | 0 | 0 | 0 | 0 | 0 | 1 |
| 1 | 1 | 0 | 0 | 1 | 1 | 1 | 0 | 1 | 0 | 0 | 0 | 0 | 0 | 1 |
| 1 | 1 | 0 | 0 | 1 | 1 | 1 | 1 | 0 | 0 | 0 | 0 | 0 | 0 | 1 |
| 1 | 1 | 0 | 0 | 1 | 1 | 1 | 1 | 1 | 0 | 0 | 0 | 0 | 0 | 1 |
| 1 | 1 | 0 | 1 | 0 | 0 | 0 | 0 | 0 | 0 | 0 | 0 | 0 | 1 | X |
| 1 | 1 | 0 | 1 | 0 | 0 | 0 | 0 | 1 | 0 | 0 | 0 | 0 | 1 | X |
| 1 | 1 | 0 | 1 | 0 | 0 | 0 | 1 | 0 | 0 | 0 | 0 | 0 | 1 | X |
| 1 | 1 | 0 | 1 | 0 | 0 | 0 | 1 | 1 | 0 | 0 | 0 | 0 | 1 | X |
| 1 | 1 | 0 | 1 | 0 | 0 | 1 | 0 | 0 | 0 | 0 | 0 | 0 | 1 | X |
| 1 | 1 | 0 | 1 | 0 | 0 | 1 | 0 | 1 | 0 | 0 | 0 | 0 | 1 | X |
| 1 | 1 | 0 | 1 | 0 | 0 | 1 | 1 | 0 | 0 | 0 | 0 | 0 | 1 | X |
| 1 | 1 | 0 | 1 | 0 | 0 | 1 | 1 | 1 | 0 | 0 | 0 | 0 | 1 | X |
| 1 | 1 | 0 | 1 | 0 | 1 | 0 | 0 | 0 | 0 | 0 | 0 | 0 | 1 | X |
| 1 | 1 | 0 | 1 | 0 | 1 | 0 | 0 | 1 | 0 | 0 | 0 | 0 | 1 | X |
| 1 | 1 | 0 | 1 | 0 | 1 | 0 | 1 | 0 | 0 | 0 | 0 | 0 | 1 | X |
| 1 | 1 | 0 | 1 | 0 | 1 | 0 | 1 | 1 | 0 | 0 | 0 | 0 | 1 | X |
| 1 | 1 | 0 | 1 | 0 | 1 | 1 | 0 | 0 | 0 | 0 | 0 | 0 | 1 | X |
| 1 | 1 | 0 | 1 | 0 | 1 | 1 | 0 | 1 | 0 | 0 | 0 | 0 | 1 | X |
| 1 | 1 | 0 | 1 | 0 | 1 | 1 | 1 | 0 | 0 | 0 | 0 | 0 | 1 | X |
| 1 | 1 | 0 | 1 | 0 | 1 | 1 | 1 | 1 | 0 | 0 | 0 | 0 | 1 | X |
| 1 | 1 | 0 | 1 | 1 | 0 | 0 | 0 | 0 | 0 | 1 | 1 | 0 | 1 | X |
| 1 | 1 | 0 | 1 | 1 | 0 | 0 | 0 | 1 | 0 | 1 | 1 | 0 | 1 | X |
| 1 | 1 | 0 | 1 | 1 | 0 | 0 | 1 | 0 | 0 | 1 | 1 | 0 | 1 | X |
| 1 | 1 | 0 | 1 | 1 | 0 | 0 | 1 | 1 | 0 | 1 | 1 | 0 | 1 | X |
| 1 | 1 | 0 | 1 | 1 | 0 | 1 | 0 | 0 | 0 | 1 | 1 | 0 | 1 | X |
| 1 | 1 | 0 | 1 | 1 | 0 | 1 | 0 | 1 | 0 | 1 | 1 | 0 | 1 | X |
| 1 | 1 | 0 | 1 | 1 | 0 | 1 | 1 | 0 | 0 | 1 | 1 | 0 | 1 | X |
| 1 | 1 | 0 | 1 | 1 | 0 | 1 | 1 | 1 | 0 | 1 | 1 | 0 | 1 | X |
| 1 | 1 | 0 | 1 | 1 | 1 | 0 | 0 | 0 | 0 | 1 | 1 | 0 | 1 | X |
| 1 | 1 | 0 | 1 | 1 | 1 | 0 | 0 | 1 | 0 | 1 | 1 | 0 | 1 | X |
| 1 | 1 | 0 | 1 | 1 | 1 | 0 | 1 | 0 | 0 | 1 | 1 | 0 | 1 | X |
| 1 | 1 | 0 | 1 | 1 | 1 | 0 | 1 | 1 | 0 | 1 | 1 | 0 | 1 | X |
| 1 | 1 | 0 | 1 | 1 | 1 | 1 | 0 | 0 | 0 | 1 | 1 | 0 | 1 | X |
| 1 | 1 | 0 | 1 | 1 | 1 | 1 | 0 | 1 | 0 | 1 | 1 | 0 | 1 | X |
| 1 | 1 | 0 | 1 | 1 | 1 | 1 | 1 | 0 | 0 | 1 | 1 | 0 | 1 | X |
| 1 | 1 | 0 | 1 | 1 | 1 | 1 | 1 | 1 | 0 | 1 | 1 | 0 | 1 | X |
| 1 | 1 | 1 | 0 | 0 | 0 | 0 | 0 | 0 | 0 | 0 | 0 | 0 | 1 | X |
| 1 | 1 | 1 | 0 | 0 | 0 | 0 | 0 | 1 | 0 | 0 | 0 | 0 | 1 | X |
| 1 | 1 | 1 | 0 | 0 | 0 | 0 | 1 | 0 | 0 | 0 | 0 | 0 | 1 | X |
| 1 | 1 | 1 | 0 | 0 | 0 | 0 | 1 | 1 | 0 | 0 | 0 | 0 | 1 | X |
| 1 | 1 | 1 | 0 | 0 | 0 | 1 | 0 | 0 | 0 | 0 | 0 | 0 | 1 | X |
| 1 | 1 | 1 | 0 | 0 | 0 | 1 | 0 | 1 | 0 | 0 | 0 | 0 | 1 | X |
| 1 | 1 | 1 | 0 | 0 | 0 | 1 | 1 | 0 | 0 | 0 | 0 | 0 | 1 | X |
| 1 | 1 | 1 | 0 | 0 | 0 | 1 | 1 | 1 | 0 | 0 | 0 | 0 | 1 | X |
| 1 | 1 | 1 | 0 | 0 | 1 | 0 | 0 | 0 | 0 | 0 | 0 | 0 | 1 | X |
| 1 | 1 | 1 | 0 | 0 | 1 | 0 | 0 | 1 | 0 | 0 | 0 | 0 | 1 | X |
| 1 | 1 | 1 | 0 | 0 | 1 | 0 | 1 | 0 | 0 | 0 | 0 | 0 | 1 | X |
| 1 | 1 | 1 | 0 | 0 | 1 | 0 | 1 | 1 | 0 | 0 | 0 | 0 | 1 | X |
| 1 | 1 | 1 | 0 | 0 | 1 | 1 | 0 | 0 | 0 | 0 | 0 | 0 | 1 | X |
| 1 | 1 | 1 | 0 | 0 | 1 | 1 | 0 | 1 | 0 | 0 | 0 | 0 | 1 | X |
| 1 | 1 | 1 | 0 | 0 | 1 | 1 | 1 | 0 | 0 | 0 | 0 | 0 | 1 | X |
| 1 | 1 | 1 | 0 | 0 | 1 | 1 | 1 | 1 | 0 | 0 | 0 | 0 | 1 | X |

-continued

| P3 | P2 | P1 | P0 | RST* | MBLIP* | SBLIP* | MDIR | SDIR | N3 | N2 | N1 | N0 | OBIP* | ODIR |
|---|---|---|---|---|---|---|---|---|---|---|---|---|---|---|
| 1 | 1 | 1 | 0 | 0 | 1 | 1 | 1 | 1 | 0 | 0 | 0 | 0 | 1 | X |
| 1 | 1 | 1 | 0 | 1 | 0 | 0 | 0 | 0 | 1 | 1 | 1 | 1 | 0 | 0 |
| 1 | 1 | 1 | 0 | 1 | 0 | 0 | 0 | 1 | 1 | 1 | 0 | 1 | 0 | 0 |
| 1 | 1 | 1 | 0 | 1 | 0 | 0 | 1 | 0 | 1 | 1 | 1 | 1 | 0 | 0 |
| 1 | 1 | 1 | 0 | 1 | 0 | 0 | 1 | 1 | 1 | 1 | 1 | 1 | 0 | 0 |
| 1 | 1 | 1 | 0 | 1 | 0 | 1 | 0 | 0 | 0 | 0 | 1 | 0 | 0 | 0 |
| 1 | 1 | 1 | 0 | 1 | 0 | 1 | 0 | 1 | 0 | 0 | 1 | 0 | 0 | 0 |
| 1 | 1 | 1 | 0 | 1 | 0 | 1 | 1 | 0 | 0 | 0 | 1 | 0 | 0 | 0 |
| 1 | 1 | 1 | 0 | 1 | 0 | 1 | 1 | 1 | 0 | 0 | 1 | 0 | 0 | 0 |
| 1 | 1 | 1 | 0 | 1 | 1 | 0 | 0 | 0 | 1 | 1 | 1 | 1 | 0 | 0 |
| 1 | 1 | 1 | 0 | 1 | 1 | 0 | 0 | 1 | 1 | 1 | 0 | 1 | 0 | 0 |
| 1 | 1 | 1 | 0 | 1 | 1 | 0 | 1 | 0 | 1 | 1 | 1 | 1 | 0 | 0 |
| 1 | 1 | 1 | 0 | 1 | 1 | 0 | 1 | 1 | 1 | 1 | 0 | 1 | 0 | 0 |
| 1 | 1 | 1 | 0 | 1 | 1 | 1 | 0 | 0 | 0 | 0 | 0 | 0 | 0 | 0 |
| 1 | 1 | 1 | 0 | 1 | 1 | 1 | 0 | 1 | 0 | 0 | 0 | 0 | 0 | 0 |
| 1 | 1 | 1 | 0 | 1 | 1 | 1 | 1 | 0 | 0 | 0 | 0 | 0 | 0 | 0 |
| 1 | 1 | 1 | 0 | 1 | 1 | 1 | 1 | 1 | 0 | 0 | 0 | 0 | 0 | 0 |
| 1 | 1 | 1 | 1 | 0 | 0 | 0 | 0 | 0 | 0 | 0 | 0 | 0 | 1 | X |
| 1 | 1 | 1 | 1 | 0 | 0 | 0 | 0 | 1 | 0 | 0 | 0 | 0 | 1 | X |
| 1 | 1 | 1 | 1 | 0 | 0 | 0 | 1 | 0 | 0 | 0 | 0 | 0 | 1 | X |
| 1 | 1 | 1 | 1 | 0 | 0 | 0 | 1 | 1 | 0 | 0 | 0 | 0 | 1 | X |
| 1 | 1 | 1 | 1 | 0 | 0 | 1 | 0 | 0 | 0 | 0 | 0 | 0 | 1 | X |
| 1 | 1 | 1 | 1 | 0 | 0 | 1 | 0 | 1 | 0 | 0 | 0 | 0 | 1 | X |
| 1 | 1 | 1 | 1 | 0 | 0 | 1 | 1 | 0 | 0 | 0 | 0 | 0 | 1 | X |
| 1 | 1 | 1 | 1 | 0 | 0 | 1 | 1 | 1 | 0 | 0 | 0 | 0 | 1 | X |
| 1 | 1 | 1 | 1 | 0 | 1 | 0 | 0 | 0 | 0 | 0 | 0 | 0 | 1 | X |
| 1 | 1 | 1 | 1 | 0 | 1 | 0 | 0 | 1 | 0 | 0 | 0 | 0 | 1 | X |
| 1 | 1 | 1 | 1 | 0 | 1 | 0 | 1 | 0 | 0 | 0 | 0 | 0 | 1 | X |
| 1 | 1 | 1 | 1 | 0 | 1 | 0 | 1 | 1 | 0 | 0 | 0 | 0 | 1 | X |
| 1 | 1 | 1 | 1 | 0 | 1 | 1 | 0 | 0 | 0 | 0 | 0 | 0 | 1 | X |
| 1 | 1 | 1 | 1 | 0 | 1 | 1 | 0 | 1 | 0 | 0 | 0 | 0 | 1 | X |
| 1 | 1 | 1 | 1 | 0 | 1 | 1 | 1 | 0 | 0 | 0 | 0 | 0 | 1 | X |
| 1 | 1 | 1 | 1 | 0 | 1 | 1 | 1 | 1 | 0 | 0 | 0 | 0 | 1 | X |
| 1 | 1 | 1 | 1 | 1 | 0 | 0 | 0 | 0 | 0 | 1 | 0 | 0 | 1 | X |
| 1 | 1 | 1 | 1 | 1 | 0 | 0 | 0 | 1 | 0 | 1 | 0 | 0 | 1 | X |
| 1 | 1 | 1 | 1 | 1 | 0 | 0 | 1 | 0 | 0 | 1 | 0 | 0 | 1 | X |
| 1 | 1 | 1 | 1 | 1 | 0 | 0 | 1 | 1 | 0 | 1 | 0 | 0 | 1 | X |
| 1 | 1 | 1 | 1 | 1 | 0 | 1 | 0 | 0 | 0 | 1 | 0 | 0 | 1 | X |
| 1 | 1 | 1 | 1 | 1 | 0 | 1 | 0 | 1 | 0 | 1 | 0 | 0 | 1 | X |
| 1 | 1 | 1 | 1 | 1 | 0 | 1 | 1 | 0 | 0 | 1 | 0 | 0 | 1 | X |
| 1 | 1 | 1 | 1 | 1 | 0 | 1 | 1 | 1 | 0 | 1 | 0 | 0 | 1 | X |
| 1 | 1 | 1 | 1 | 1 | 1 | 0 | 0 | 0 | 0 | 1 | 0 | 0 | 1 | X |
| 1 | 1 | 1 | 1 | 1 | 1 | 0 | 0 | 1 | 0 | 1 | 0 | 0 | 1 | X |
| 1 | 1 | 1 | 1 | 1 | 1 | 0 | 1 | 0 | 0 | 1 | 0 | 0 | 1 | X |
| 1 | 1 | 1 | 1 | 1 | 1 | 0 | 1 | 1 | 0 | 1 | 0 | 0 | 1 | X |
| 1 | 1 | 1 | 1 | 1 | 1 | 1 | 0 | 0 | 0 | 1 | 0 | 0 | 1 | X |
| 1 | 1 | 1 | 1 | 1 | 1 | 1 | 0 | 1 | 0 | 1 | 0 | 0 | 1 | X |
| 1 | 1 | 1 | 1 | 1 | 1 | 1 | 1 | 0 | 0 | 1 | 0 | 0 | 1 | X |
| 1 | 1 | 1 | 1 | 1 | 1 | 1 | 1 | 1 | 0 | 1 | 0 | 0 | 1 | X |

| Glossary B | |
|---|---|
| Name | Meaning |
| P3 | internal |
| P2 | internal |
| P1 | internal |
| P0 | internal |
| RST | internal |
| N3 | internal |
| N2 | internal |
| N1 | internal |
| N0 | internal |
| OBLIP | output degree count |
| ODIR | output degree direction |

The logical arrangement described herein can be best summarized as follows when the practitioner desires to measure the difference between the rotation of the master sensor and display unit 100 and rotation of the slave sensor unit 102. The master sensor and display unit 100 is used as a reference. Any relative movement between the master sensor and display unit 100 and the slave sensor unit 102 is to be displayed, therefore, if the master sensor and display unit 100 moves one degree CW and the slave sensor unit 102 doesn't move, the output is one degree. If the master sensor and display unit 100 moves one degree CW and the slave sensor unit 102 moves one degree CCW, the movement between the two is output as two degrees CW.

Still referring to FIG. 5, the count and direction output from the third PAL 180 is fed into a counter and display 182 that exhibits the resultant angles from an initial zero position. The initial zero position is defined when the zero switch 186 is activated which functions to clear the counter and display 182 to zero. It is preferred that the counter and display 182 be one available from Red Lion Controls of York, Pa. and referred to in the art as an 8 digit component counter with 6 digit LCD display. Further information regarding the preferred component for the counter and display 182 is available from Red Lion Controls in the publication entitled Sub-Cube-D—8 digit component counter with 6 digit LCD display, Bulletin No. SCUBD-1

(effective 5/88) and from U.S. Pat. No. 4,599,600, both of which are now incorporated herein by reference.

A hold switch 188 is connected to the counter and display 182. The hold switch functions to freeze the value shown by the counter and display 182 when the hold switch is activated so that the practitioner can read and note the value shown on the LCD display provided on the counter and display 182.

In view of the foregoing, it will be appreciated that the present invention provides a self contained apparatus for measuring the difference between the motion of two different regions of a patient's body. The present invention further provides a system for measuring the difference in the range of motion between two regions of a patient's body which is small, portable, and convenient to carry. The present invention also provides a system for measuring the difference between the range of motion of two regions on a patient's body which does not require lengthy cords or cables which interfere with a practitioner's use of the system and examination of the patient and which provides a system for measuring the differential of the motion of two body regions which includes an internal power supply and does not require any connection to an external power source.

The present invention also provides a system for making differential measurements of the motion of two body parts which consists of only two measuring components which are interconnected and which require no other components. The present invention also provides a dual inclinometer system for measuring range of motion which does not contain any electrical potentials which could harm a patient and which provides differential measurements between the motion of different regions of a patient's body which allows the practitioner to maintain attention directed to the patient. The present invention also provides a dual inclinometer system for measuring range of motion in a region of a patient's body which provides more easily perceived and recorded results.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for reducing the power required by an differential inclinometer system comprising:

battery means;

first housing means containing the battery means;

first incline sensing means, contained within the first housing means, for measuring the angle at which the first housing means is disposed in relation to gravity and for generating a first signal which changes its state as each increment of incline is encountered, the first incline sensing means receiving power from the battery means;

second housing means for housing a second incline sensing means, contained within the second housing means, for measuring the angle at which the second housing means is disposed in relation to gravity and for generating a second signal which changes its state as each increment of incline is encountered;

calculation means for manipulating the second signal and the first signal to arrive at a third signal, the third signal representing the difference between the first incline sensing means and the second incline sensing means;

interconnection means for conveying the first signal and the second signal to the calculation means; and means for strobing the power received by the first incline sensing means from the battery means, the power being strobed at a rate greater than the expected state changes of the signal generated by the incline sensing means.

2. A system for reducing the power required by an inclinometer as defined in claim 1 wherein the incline sensing means comprises:

an encoder wheel comprising a plurality of optically readable indicia;

means for pivotally mounting the encoder wheel to allow rotation of the encoder wheel in a first plane;

means for directing the encoder wheel in a downward orientation with respect to gravity; and means for optically sensing the passage of the optically readable indications as said indications pass by a first location as the encoder wheel rotates in the first plane.

3. A system for reducing the power required by an inclinometer as defined in claim 1 wherein the rate is at least as great as ten thousand per second.

4. A system for reducing the power required by an inclinometer as defined in claim 1 wherein the housing means comprises a housing having dimensions not greater than about four inches high, about 2.5 inches wide, and about 0.75 inches thick.

5. A system for reducing the power required by an inclinometer as defined in claim 1 wherein the battery means comprises a single dry cell having a nominal output voltage of 1.5 volts.

\* \* \* \* \*